(12) United States Patent
Kassab et al.

(10) Patent No.: US 8,480,708 B2
(45) Date of Patent: Jul. 9, 2013

(54) DEVICES, SYSTEMS, AND METHODS FOR PERCUTANEOUS TRANS-SEPTAL LEFT ATRIAL APPENDAGE OCCLUSION

(75) Inventors: Ghassan S. Kassab, Zionsville, IN (US); Jose A. Navia, Sr., Buenos Aires (AR)

(73) Assignee: CVDevices, LLC, Zionsville, IN (US)

( * ) Notice: Subject to any disclaimer, the term of this patent is extended or adjusted under 35 U.S.C. 154(b) by 221 days.

(21) Appl. No.: 12/863,540

(22) PCT Filed: Jan. 6, 2009

(86) PCT No.: PCT/US2009/030222
§ 371 (c)(1),
(2), (4) Date: Jul. 19, 2010

(87) PCT Pub. No.: WO2009/094237
PCT Pub. Date: Jul. 30, 2009

(65) Prior Publication Data
US 2010/0286718 A1 Nov. 11, 2010

Related U.S. Application Data

(63) Continuation-in-part of application No. PCT/US2008/000838, filed on Jan. 23, 2008.

(60) Provisional application No. 60/881,831, filed on Jan. 23, 2007.

(51) Int. Cl.
*A61D 1/00* (2006.01)

(52) U.S. Cl.
USPC .......................................................... 606/213

(58) Field of Classification Search
USPC ......................................... 606/191, 192, 194
See application file for complete search history.

(56) References Cited

U.S. PATENT DOCUMENTS

| 6,152,144 | A | 11/2000 | Lesh et al. |
| 6,315,709 | B1 | 11/2001 | Garibaldi et al. |

(Continued)

OTHER PUBLICATIONS

International Searching Authority, International Search Report, PCT/US2009/030222, dated Feb. 24, 2009.

(Continued)

*Primary Examiner* — Melanie Tyson
(74) *Attorney, Agent, or Firm* — Reichel IP LLP; Mark C. Reichel; Kevin R. Erdman

(57) ABSTRACT

Methods for occluding an atrial appendage. The steps of an exemplary method include introducing at least a portion of the first device in a heart, introducing at least a portion of a second device into a pericardial space surrounding the heart, positioning the balloon of the first device at least partially within an atrial appendage cavity, inflating the balloon to displace blood present within the atrial appendage cavity, positioning the loop of the second device around the atrial appendage, tightening the loop around the atrial appendage, deflating the balloon to allow for ultimate removal of the first device from the atrial appendage cavity, and separating the loop from the second device so that the loop remains positioned and tightened around the atrial appendage.

20 Claims, 32 Drawing Sheets

U.S. PATENT DOCUMENTS

| | | | |
|---|---|---|---|
| 7,918,865 B2 * | 4/2011 | Liddicoat et al. | 606/139 |
| 2003/0120337 A1 | 6/2003 | Van Tassel et al. | |
| 2005/0090861 A1 | 4/2005 | Porter | |
| 2005/0096501 A1 | 5/2005 | Stelzer et al. | |
| 2006/0020271 A1 | 1/2006 | Stewart et al. | |
| 2006/0036284 A1 | 2/2006 | Bleaser et al. | |
| 2006/0253129 A1 | 11/2006 | Liddicoat et al. | |
| 2007/0233239 A1 | 10/2007 | Navia et al. | |

OTHER PUBLICATIONS

International Searching Authority (ISA), Written Opinion of the ISA, PCT/US2009/030222, dated Feb. 24, 2009.

International Searching Authority, International Search Report, PCT/US2008/000838, dated Jul. 8, 2008.

International Searching Authority (ISA), Written Opinion of the ISA, PCT/US2008/000838, dated Jul. 8, 2008.

* cited by examiner

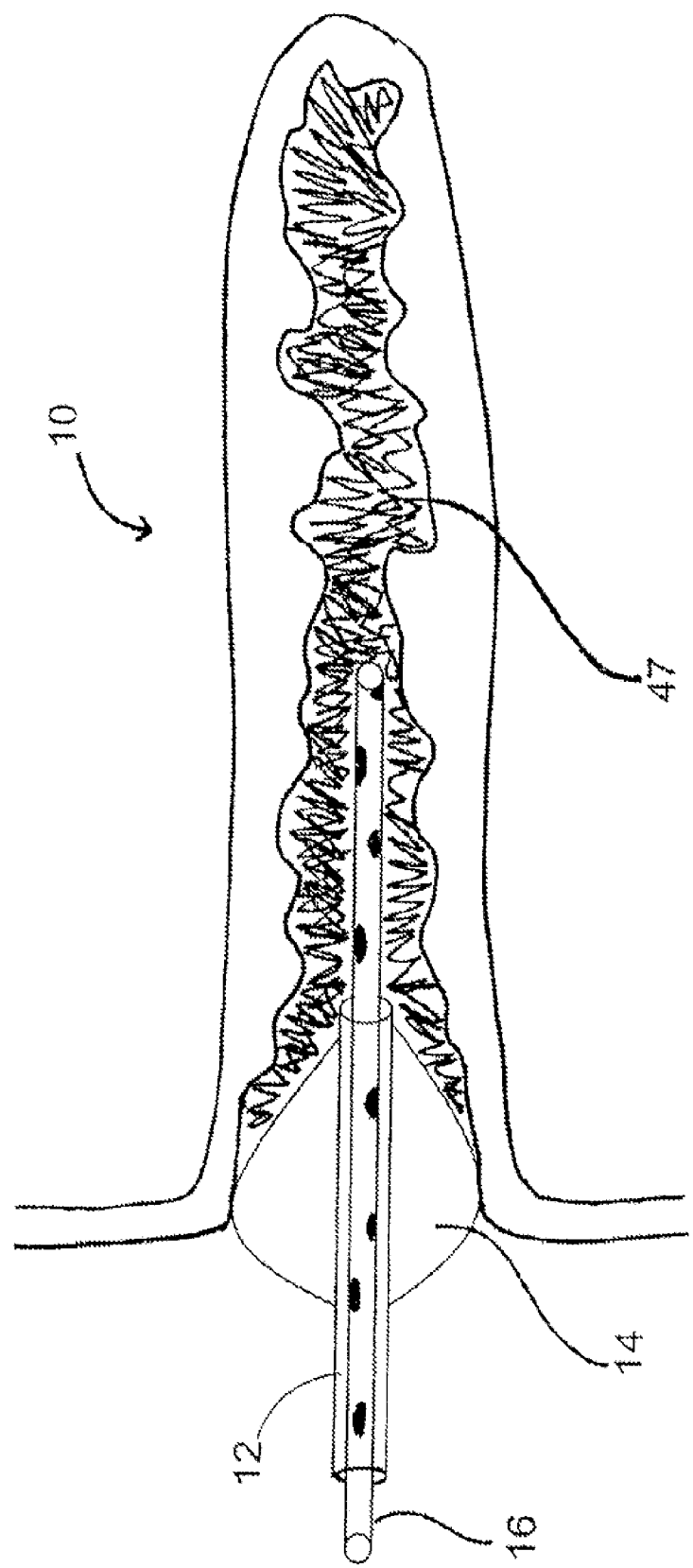

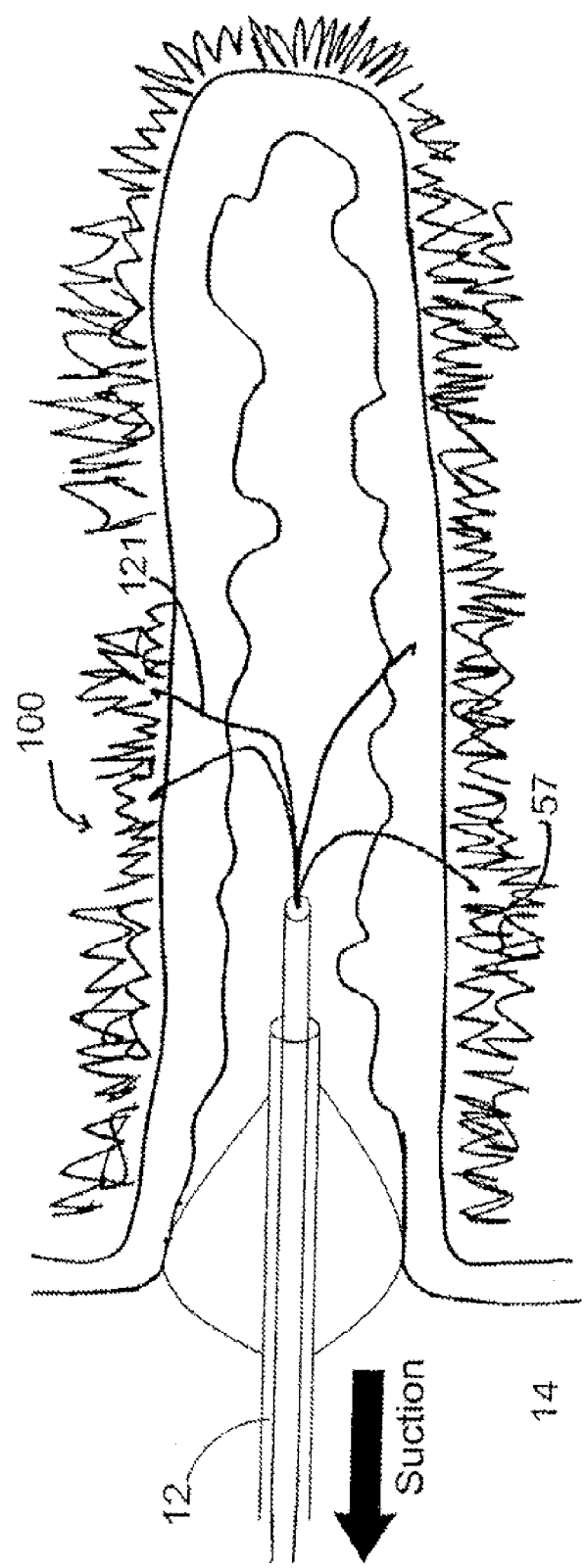

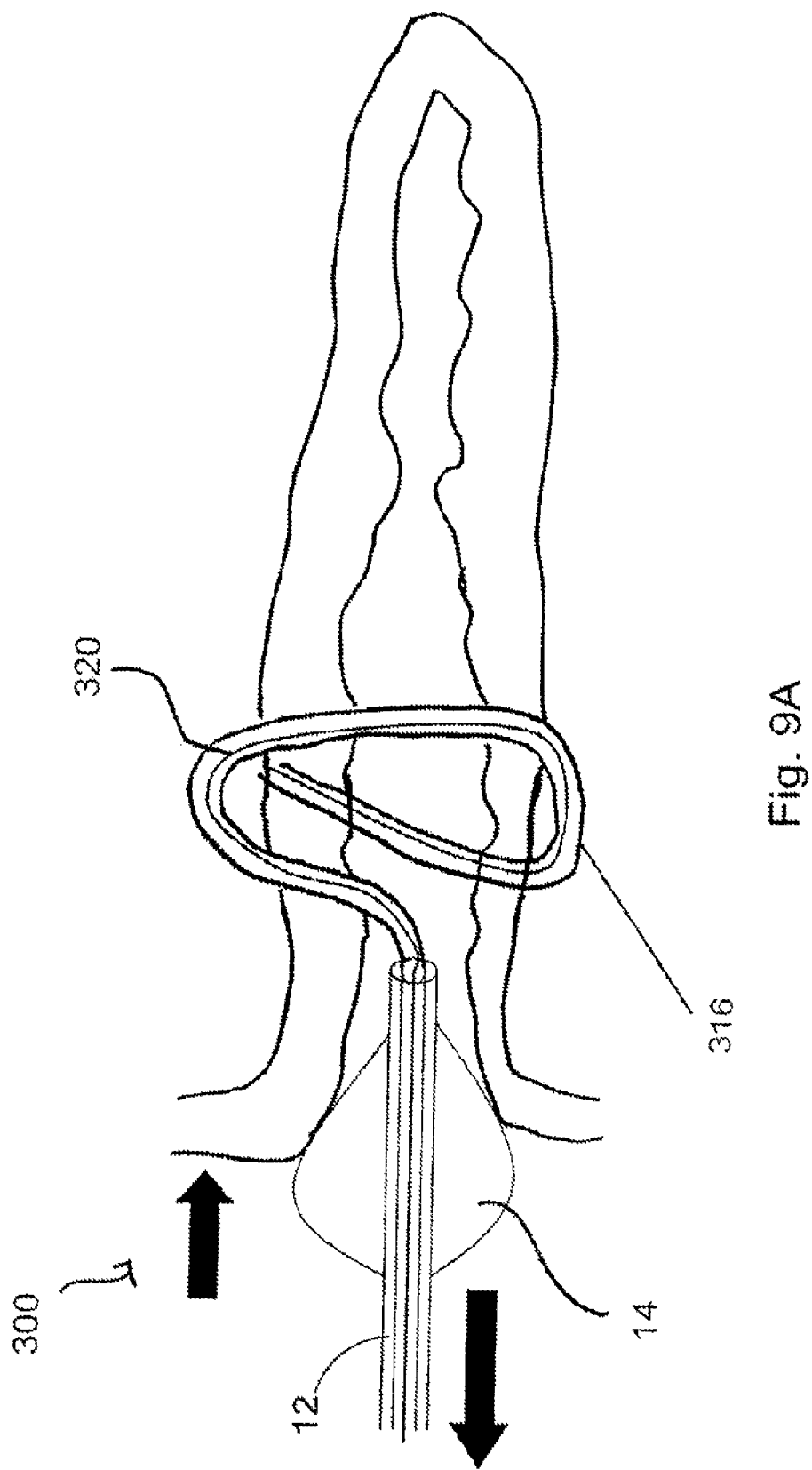

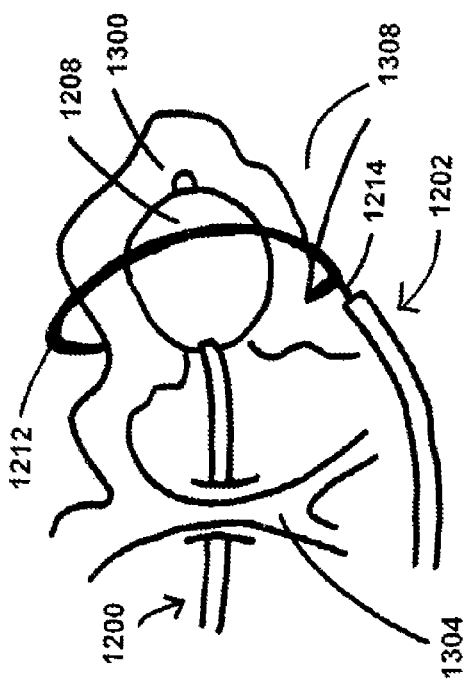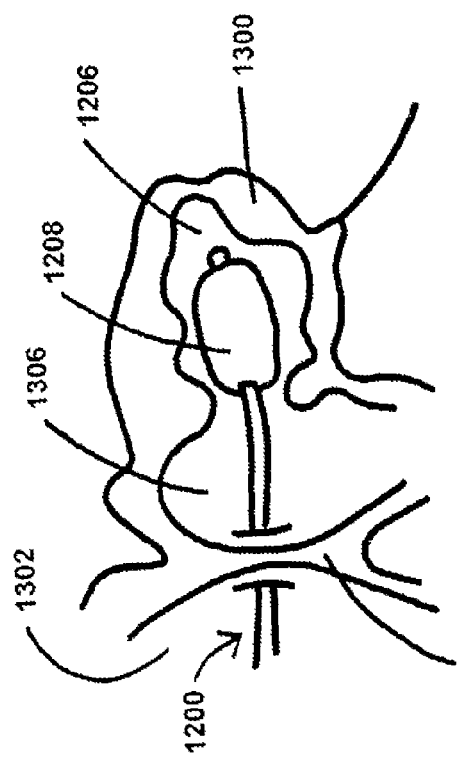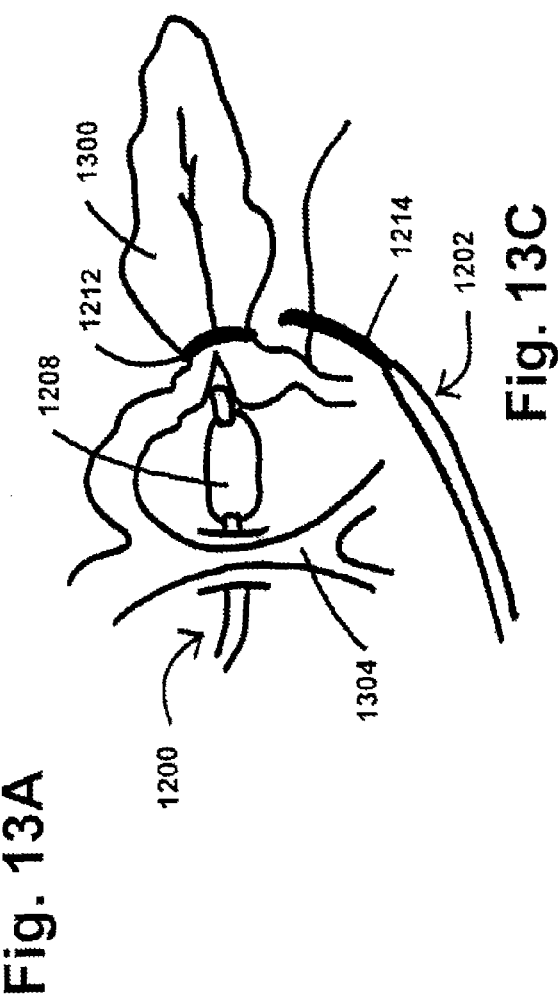

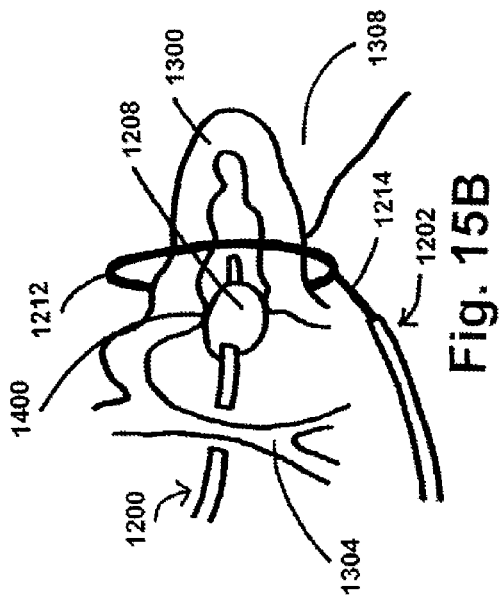
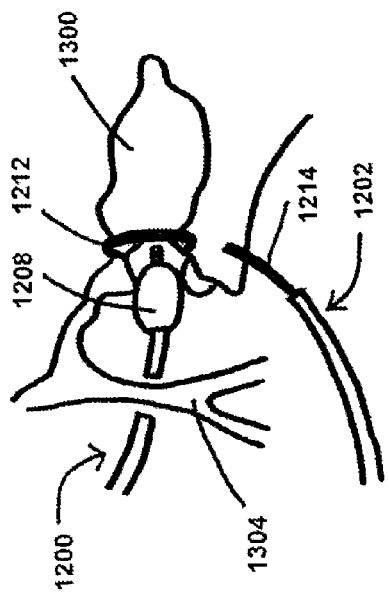
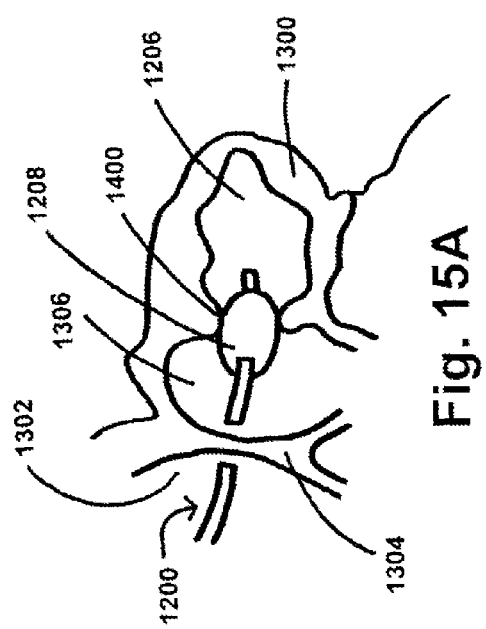

DEVICES, SYSTEMS, AND METHODS FOR PERCUTANEOUS TRANS-SEPTAL LEFT ATRIAL APPENDAGE OCCLUSION

PRIORITY

The present application is related to, and claims the priority benefit of, International Patent Application Serial No. PCT/US2009/030222, filed Jan. 6, 2009, which is related to, is a continuation-in-part application of, and claims the priority benefit of, International Patent Application Serial No. PCT/US2008/000838, filed Jan. 23, 2008, which is related to, and claims the priority benefit of, U.S. Provisional Patent Application Ser. No. 60/881,831, filed Jan. 23, 2007. The contents of each of these applications are hereby incorporated by reference in their entirety into this disclosure.

BACKGROUND

Currently, 2.2 million patients in the United States suffer atrial fibrillation ("AF"). About half of these patients are considered to be at a high risk for stroke. The Stroke Prevention in Atrial Fibrillation trials (SPAF, SPAF II, SPAF III) have shown that chronic warfarin therapy reduces the risk of stroke by about 70%. Nevertheless, problems related with the long term use of anti-coagulation treatments are well known. It has been shown that up to two-thirds of eligible AF patients do not receive warfarin treatment. This can be at least partly attributed to the fact that warfarin is difficult to dose as it is known to interact with many commonly-used medications and other chemicals that may be present in appreciable quantities in food. Accordingly, safer options are desirable.

AF is frequently diagnosed in elderly patients and is responsible for more than 15% of all strokes. This percentage grows to almost 25% in women and men older than 80 years of age. Dilation of the left atrium and a reduction of blood flow velocity, especially in the left atrial appendage, is commonly seen with AF. Atrial contraction is responsible for blood ejection out of the left atrium and appendage. The dysfunction of the left atrial contraction is followed by blood stagnation, especially at the level of the atrial appendage. It has been demonstrated by means of echocardiography and autopsy studies that more than 90% of all thrombi in patients with non-rheumatic AF beginning in the left atrium, appear in the left atrial appendage. Thrombus formation elevates the threat of stroke by three-fold.

The left atrial appendage ("LAA") is an embryonic remnant of the left atrium that grows during the third week of pregnancy. The left atrial cavity develops soon after and is produced from an outgrowth of the pulmonary veins. The diameter of the LAA ostium into the left atrial cavity is about 1 to 4 cm and is positioned between the left upper pulmonary vein and the left ventricle. The left axis deviation orifice, width, and length are typically about 0.7 to 2 cm, 0.9 to 3.4 cm, and 1.3 to 4 cm, respectively. The circumflex branch and the left coronary artery runs close to the base of the LAA ostium.

The LAA is a long structure with tubular or hooked shape of variable morphology and size. The LAA wall is trabeculated including muscle bars, known as pectinate muscles. The cavities between the pectinate muscles emerge as "branches" (lobes), "twigs", or "fine structures." LAA closure may be an option in patients who cannot receive anticoagulation treatment as a result of contraindications or conditions in which the hemorrhage risk is greater than the potential medical benefit.

One of the convention options of treating LAA closure is surgery. However, it is unsuitable for the same high-risk patients who are poor candidates for warfarin therapy. Accordingly, a safe, accurate and minimally invasive procedure is needed to occlude the LAA.

BRIEF SUMMARY

Embodiments disclosed herein comprise devices and methods of LAA occlusion that do not require surgery and avoid many of the risks associated with current methods of LAA occlusion.

In at least one embodiment of a system useful for occluding an atrial appendage of a heart, the system comprises a first device comprising a first tube sized and shaped for insertion into the heart and a balloon coupled to the first tube, wherein the balloon is capable of inflation and deflation, a second device comprising a second tube sized and shaped for insertion into a pericardial space surrounding the heart, the second tube comprising a lumen extending at least partially from a second tube distal end to a second tube proximal end, and a loop sized and shaped to fit at least partially within the lumen of the second tube, wherein the loop is capable of protraction from the second tube distal end, wherein the loop of the second device is capable of being placed around the atrial appendage and secured around the atrial appendage.

In another embodiment, the second device further comprises a shaft having a distal end, wherein the loop is coupled to the shaft at or near the distal end of the shaft. In yet another embodiment, at least one aperture is defined within the first tube at or near the balloon, the at least one aperture sized and shaped to allow a gas and/or a liquid to be introduced and/or removed from the balloon. In an additional embodiment, the balloon of the first device, when inserted into an atrial appendage cavity, is capable of inflation to displace blood present within the atrial appendage cavity. In yet an additional embodiment, the balloon of the first device, when positioned at an entrance of an atrial appendage cavity, is capable of inflation to occlude the entrance of the atrial appendage cavity, and wherein suction from a suction source operably coupled to the first tube facilitates the removal of blood present within the atrial appendage cavity.

In at least one embodiment of a system useful for occluding an atrial appendage of a heart, the system further comprises a first guide wire useful to facilitate the insertion of the first tube of the first device into the heart. In an additional embodiment, the system further comprises a second guide wire useful to facilitate the insertion of the second tube of the second device into the pericardial space surrounding the heart. In yet an additional embodiment, the first guide wire and the second guide wire are the same guide wire. In another embodiment, the balloon is sized and shaped to fit within an atrial appendage cavity. In yet another embodiment, the balloon is sized and shaped to fit within an entrance to an atrial appendage cavity.

In at least one embodiment of a system useful for occluding an atrial appendage of a heart, the system comprises a first device comprising a first tube sized and shaped for insertion into the heart and a balloon coupled to the first tube, wherein the balloon is capable of inflation and deflation, and a second device comprising a second tube sized and shaped for insertion into a pericardial space surrounding the heart, the second tube comprising a lumen extending at least partially from a second tube distal end to a second tube proximal end, a loop sized and shaped to fit at least partially within the lumen of the second tube, wherein the loop is capable of protraction from the second tube distal end, and a shaft having a distal end, wherein the loop is coupled to the shaft at or near the distal end of the shaft, wherein the loop of the second device is capable of being placed around an atrial appendage and secured around the atrial appendage.

In at least one embodiment of a method for occluding an atrial appendage of a heart, the method comprises the steps of introducing at least a portion of a first device into an atrial appendage cavity of a heart, the first device comprising a first tube having a distal end and a balloon capable of inflation and deflation, the balloon coupled to the first tube at or near the distal end of the first tube, introducing at least a portion of a second device into a pericardial space surrounding the heart, the second device comprising a second tube sized and shaped for insertion into the pericardial space surrounding the heart, the second tube comprising a lumen extending at least partially from a second tube distal end to a second tube proximal end and a loop sized and shaped to fit at least partially within the lumen of the second tube, wherein the loop is capable of protraction from the second tube distal end, positioning the balloon of the first device at least partially within the atrial appendage cavity, inflating the balloon to displace blood present within the atrial appendage cavity, positioning the loop of the second device around the atrial appendage, tightening the loop around the atrial appendage, deflating the balloon to allow for ultimate removal of the first device from the atrial appendage cavity, and separating the loop from the second device so that the loop remains positioned and tightened around the atrial appendage.

In another embodiment of a method for occluding an atrial appendage of a heart of a patient, the method comprises the steps of providing a first device, the first device comprising a first tube having a distal end and a balloon capable of inflation and deflation, the balloon coupled to the first tube at or near the distal end of the first tube, the balloon sized and shaped for insertion into a left atrial appendage cavity, providing a second device, the second device comprising a second tube sized and shaped for insertion into a pericardial space surrounding the heart, the second tube comprising a lumen extending at least partially from a second tube distal end to a second tube proximal end, a loop sized and shaped to fit at least partially within the lumen of the second tube, wherein the loop is capable of protraction from the second tube distal end, and a shaft having a distal end, wherein the loop is coupled to the shaft at or near the distal end of the shaft, introducing the first device into the patient using femoral or jugular venous puncture, advancing the first device within the patient from a site of femoral or jugular venous puncture so that the distal end of the first tube of the first device is positioned within a right atrium of the heart, puncturing a septum between the right atrium and a left atrium of the heart using the first device, advancing the distal end of the first tube of the first device through the punctured septum, positioning the distal end of the first tube within the left atrial appendage cavity so that the balloon is at least partially positioned within the left atrial appendage cavity, introducing the second device into the patient, advancing the second device within the patient to a location at or near a targeted tissue on an interior wall of the heart, puncturing the targeted tissue using the second device, advancing the distal end of the second tube of the second device through the punctured targeted tissue into a pericardial space to a location at or near the left atrial appendage, inflating the balloon to displace blood present within the left atrial appendage cavity, positioning the loop of the second device around the left atrial appendage, tightening the loop around the left atrial appendage, deflating the balloon to allow for ultimate removal of the first device from the left atrial appendage cavity, and separating the loop from the shaft so that the loop remains positioned and tightened around the left atrial appendage.

In at least one method for occluding an atrial appendage of a heart of a patient, the method comprises the steps of introducing at least a portion of a first device into an entrance of an atrial appendage cavity, the first device comprising a first tube having a proximal end and a distal end and a balloon capable of inflation and deflation, the balloon coupled to the first tube at or near the distal end of the first tube, introducing at least a portion of a second device into a pericardial space surrounding the heart, the second device comprising a second tube sized and shaped for insertion into the pericardial space surrounding the heart, the second tube comprising a lumen extending at least partially from a second tube distal end to a second tube proximal end and a loop sized and shaped to fit at least partially within the lumen of the second tube, wherein the loop is capable of protraction from the second tube distal end, positioning the balloon of the first device at least partially within the entrance of the atrial appendage cavity, inflating the balloon to substantially prevent blood from flowing in or out of the atrial appendage cavity, applying suction from the proximal end of the first tube to displace blood residing within the atrial appendage cavity, positioning the loop of the second device around the left atrial appendage, tightening the loop around the left atrial appendage, deflating the balloon to allow for ultimate removal of the first device from the entrance of the atrial appendage cavity, and separating the loop from the shaft so that the loop remains positioned and tightened around the left atrial appendage.

In another method for occluding an atrial appendage of a heart of a patient, the method comprises the steps of providing a first device, the first device comprising a first tube having a distal end and a balloon capable of inflation and deflation, the balloon coupled to the first tube at or near the distal end of the first tube, the balloon sized and shaped for insertion into an entrance of a left atrial appendage cavity, providing a second device, the second device comprising a second tube sized and shaped for insertion into a pericardial space surrounding the heart, the second tube comprising a lumen extending at least partially from a second tube distal end to a second tube proximal end, a loop sized and shaped to fit at least partially within the lumen of the second tube, wherein the loop is capable of protraction from the second tube distal end, and a shaft having a distal end, wherein the loop is coupled to the shaft at or near the distal end of the shaft, introducing the first device into the patient using femoral or jugular venous puncture, advancing the first device within the patient from a site of femoral or jugular venous puncture so that the distal end of the first tube of the first device is positioned within a right atrium of the heart, puncturing a septum between the right atrium and a left atrium of the heart using the first device, advancing the distal end of the first tube of the first device through the punctured septum, positioning the distal end of the first tube at the entrance of the left atrial appendage cavity so that the balloon is at least partially positioned within the entrance of the left atrial appendage cavity, introducing the second device into the patient, advancing the second device within the patient to a location at or near a targeted tissue on an interior wall of the heart, puncturing the targeted tissue using the second device, advancing the distal end of the second tube of the second device through the punctured targeted tissue into a pericardial space to a location at or near the left atrial appendage, inflating the balloon to substantially prevent blood from flowing in or out of the left atrial appendage cavity, applying suction from the proximal end of the first tube to displace blood residing within the left atrial appendage cavity, positioning the loop of the second device around the left atrial appendage, tightening the loop around the left atrial appendage, deflating the balloon to allow for ultimate removal of the first device from the entrance of the atrial appendage cavity, and separating the loop from the shaft so that the loop remains positioned and tightened around the atrial appendage.

In another embodiment, the method further comprises the step of removing the first device from the heart. In yet another embodiment, the method further comprises the step of removing the second tube from the pericardial space surrounding the heart. In an additional embodiment, the step of introducing at least a portion of a first device into an atrial appendage cavity is performed after the patient has been administered local anesthesia. In yet an additional embodiment, the step of introducing at least a portion of a first device into an atrial appendage cavity is performed after the patient has been administered a sedative allowing the patient to remain conscious as the method for occluding the atrial appendage is performed.

In at least one method for occluding an atrial appendage of a heart of a patient, the step of introducing at least a portion of a first device into an atrial appendage cavity and the step of introducing at least a portion of the second device into a pericardial space surrounding the heart are performed using transesophageal echocardiography and fluoroscopy. In another embodiment, the step of introducing at least a portion of a first device into an atrial appendage cavity is performed by inserting at least a portion of the first device into the patient using femoral venous puncture and advancing at least a portion of the first device to the heart. In yet another embodiment, the step of introducing at least a portion of a first device into an atrial appendage cavity is performed by insetting at least a portion of the first device into the patient using jugular venous puncture and advancing the first device to the heart. In an additional embodiment, the step of introducing at least a portion of a first device into an atrial appendage cavity involves a transseptal puncture from a right atrium to a left atrium of the heart. In yet an additional embodiment, the patient is administered heparin prior to the transseptal puncture.

In at least one method for occluding an atrial appendage of a heart of a patient, the step of introducing at least a portion of a first device into an atrial appendage cavity is performed using a guide wire. In another embodiment, the step of deflating the balloon allows the loop to further tighten around the atrial appendage. In yet another embodiment, the step of separating the loop from the shaft is performed using an electromagnetic current. In an additional embodiment, the step of separating the loop from the shaft is performed by twisting the shaft in a direction to allow the loop to separate from the shaft. In yet an additional embodiment, the method further comprises the step of providing the patient with an anti-platelet adhesive treatment.

In at least one method for occluding an atrial appendage of a heart of a patient, the balloon sized and shaped for insertion into the atrial appendage cavity. In another embodiment, the atrial appendage is a left atrial appendage. In yet another embodiment, the second device further comprises a shaft having a distal end, wherein the loop is coupled to the shaft at or near the distal end of the shaft. In an additional embodiment, at least one aperture is defined within the first tube at or near the balloon, and wherein the step of inflating the balloon is performed using an inflation source operably coupled to the first tube.

BRIEF DESCRIPTION OF THE DRAWINGS

FIGS. 2A-2E shows a side view of the occlusion assembly of FIGS. 1A and 1B as applied to treat a left atrial appendage;

FIGS. 3B-D shows side views of the needle wires of the occlusion assembly of FIG. 3A applied to treat a left atrial appendage;

FIGS. 7-9B shows a side view of the pigtail catheter of FIGS. 6A-6C as applied to treat a left atrial appendage.

FIG. 13A shows a view of a portion of a heart with a balloon of a first device positioned within an atrial appendage cavity;

FIG. 13B shows a view of a portion of a heart with an inflated balloon of a first device positioned within an atrial appendage cavity and a loop of a second device positioned around an atrial appendage;

FIG. 13C shows a view of a portion of a heart with a loop of a second device secured around an atrial appendage;

FIG. 15A shows a view of a portion of a heart with a balloon of a first device positioned at the opening of an atrial appendage cavity;

FIG. 15B shows a view of a portion of a heart with an inflated balloon of a first device positioned at the opening of an atrial appendage cavity and a loop of a second device positioned around an atrial appendage;

FIG. 15C shows a view of a portion of a heart with a loop of a second device secured around an atrial appendage;

DETAILED DESCRIPTION

Figure 1A:
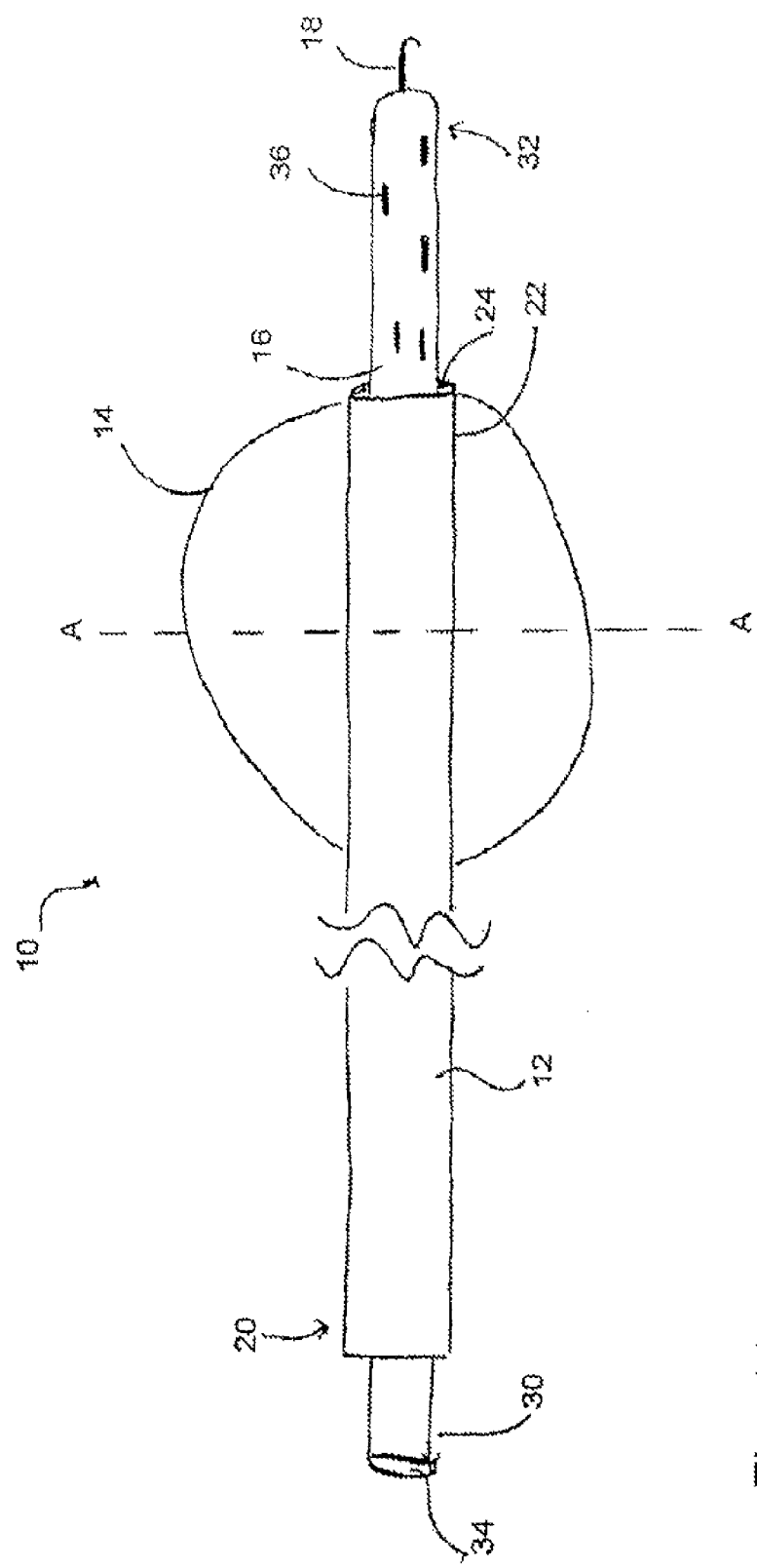
FIG. 1A shows a side view of at least one embodiment of an occlusion assembly.

Reference will now be made to the embodiments illustrated in the drawings and specific language will be used to describe the same. It will nevertheless be understood that no limitation of scope is intended by the description of these embodiments.

FIG. 1A shows a side view of one embodiment of an occlusion assembly 10 for closing a left atrial appendage. Specifically, the assembly 10 is configured for placement within the left atrial appendage ("LAA") and is delivered non-surgically through the use of catheterization and percutaneous transluminal access.

The occlusion assembly 10 comprises a shaft 12, a balloon 14, a catheter 16, and a guidewire 18. The shaft 12 comprises an elongated catheter shaft having a proximal end 20, a distal end 22, and an interior 24. Both the proximal end 20 and the distal end 22 of the shaft 12 are open and in communication with the interior 24. The interior 24 of the shaft 12 extends throughout the length of the shaft 12 and provides a channel through which the distal end 22 of the shaft 12 may be accessed when positioned within a body.

The balloon 14 is coupled with the distal end 22 of the shaft 12 and can comprise any balloon catheter tip known in the art. The balloon 14 may comprise a tube or other inflation means (not shown) coupled therewith to facilitate the inflation and deflation of the balloon 14 when positioned within the body. The balloon 14 can be configured in a range of sizes to accommodate the anatomy of the left atrial appendage. In one embodiment, the balloon 14 comprises a flattened-disk configuration, however it will be understood that the balloon 14 can comprise various shapes and forms that will assist in the temporary closing and sealing of the LAA cavity, including, without limitation, a hemisphere shape and a wine-bottle cork shape.

The occlusion assembly 10 further comprises a guidewire 18. The guidewire 18 is configured to be inserted through the interior 24 of the shaft 12 and may be any standard guidewire known in the art. In one embodiment, the guidewire 18 functions to facilitate navigation of the shaft 12 and catheter 16 into the LAA. Use of the guidewire 18 enables more effective navigation of the occlusion assembly 10 and prevents damage to the atrial or appendage walls.

In one approach, the procedure can be performed under local anesthesia and conscious sedation. The shaft 12 and the balloon 14 coupled therewith are inserted through the femoral vein and advanced to the right atrium of the heart. Thereafter, a trans-septal puncture is made at the level of the fossa ovalis area to access the left atrium. After the shaft 12 and the balloon 14 are positioned within the left atrium, the guidewire 18 is inserted into the LAA, visualized by fluoroscopy or transesophageal echocardiography, and the shaft 12 is threaded over the guidewire 18 such that the balloon 14 is positioned adjacent to the ostium of the LAA. When the balloon 14 is properly positioned, as shown in FIG. 1A, the balloon 14 is inflated to occlude the LAA orifice.

After the shaft 12 and the balloon 14 are properly positioned with respect to the LAA, the catheter 16 may be introduced. The catheter 16 of the occlusion assembly 10 comprises an elongated, flexible tube having an exterior waft, a proximal end 30, a distal end 32, a hollow interior 34, and at least one opening 36 disposed through the exterior wall. The proximal end 30 of the catheter 16 is in communication with the interior 34, and the interior 34 extends throughout the length of the catheter 16. Accordingly, the interior 34 of the catheter 16 provides a channel through which the distal end 32 may be accessed.

The catheter 16 is configured to be slidably positioned within the interior 24 of the shaft 12. For example, the distal end 32 of the catheter 16 can be inserted into the proximal end 20 of the shaft 12, advanced through the interior 24 of the shaft 12, and extended into the LAA cavity. In one embodiment, the catheter 16 comprises a length that is greater than the length of the shaft 12 such that the distal end 32 of the catheter 16 can conveniently be extended through the distal end 22 of the shaft and into the LAA cavity. Further, in at least one embodiment, the catheter 16 comprises a three-lumen pigtail catheter, such that the distal end 32 is tightly curled. This tightly curled configuration functions to prevent trauma in the event the proximal end 32 comes into contact with a vessel or organ wall as the catheter 16 is advanced through the body of a patient.

The distal end 32 of the catheter 16 comprises at least one opening 36 disposed therein. Each of openings 36 located on the distal end 32 is in communication with the interior 34 of the catheter 16 and comprises a configuration such that a force or substance can be transmitted therethrough. For example, in one embodiment, the at least one opening 36 comprises a suction port configured to aspirate an area adjacent to the catheter 16 when the at least one opening 36 is coupled with a vacuum source. In an alternative embodiment, the at least one opening 36 comprises a single opening at the distal end 32 of the catheter 16, configured such that the guidewire 18 or other device can be positioned therethrough. In yet another embodiment, the at least one opening 36 is configured to deliver a substance to the surrounding tissue, such as an adhesive or medicament. The number of openings 36 located on the distal end 32 of the catheter 16 may depend on the desired functionality of the occlusion assembly 10, and it will be understood that any number of openings 36 may be employed.

As previously described, the interior 34 of the catheter 16 extends from the proximal end 30 of the catheter 16 to the distal end 32 of the catheter 16. Further, the interior 34 is in communication with the at least one opening 36. Accordingly, the interior 34 of the catheter 16 can function as a conduit through which a force, device, and/or substance may be delivered to the at least one opening 36. For example, when a vacuum source, such as a syringe or other vacuum source, is coupled with the proximal end 30 of the catheter 16, the suctional force produced thereby can be communicated throughout the interior 34 of the catheter 16 and through the at least one opening 36 in communication therewith. In one embodiment, a syringe or other vacuum source (not shown) may be coupled with the proximal end 30 of the catheter 16 in order to provide appropriate suction throughout the interior 34 of the catheter 16. It will be understood that any type of vacuum source may be used to supply suction throughout the interior 34, such as a controlled vacuum system providing specific suction pressures. In another embodiment, an adhesive delivery device (not shown) is coupled with the proximal end 30 of the catheter 16. The adhesive delivery device may comprise any means for advancing an adhesive through the interior 34 of the catheter and through the at least one opening 36. For example, in one embodiment, the adhesive delivery device may be a clinician's hand when he or she applies force to a container of adhesive such that the adhesive is advanced through the interior 34 of the catheter 16. In an alternative embodiment, the adhesive delivery device may comprise a specifically designed mechanism for advancing the adhesive.

Figure 1B:
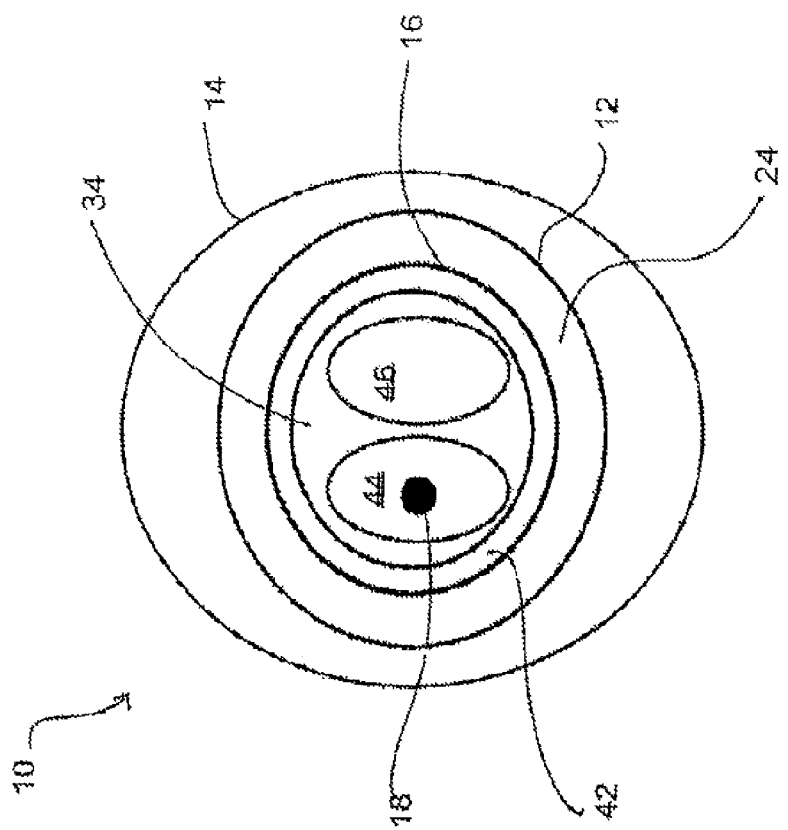
FIG. 1B shows a cross-sectional view of at least one embodiment of an occlusion assembly taken along line A-A of FIG. 1A.

Referring now to FIG. 1B, in one embodiment, the interior 34 of the catheter 16 comprises multiple lumens. In the embodiment shown in FIG. 1B, the occlusion assembly 10 comprises a triple-lumen pigtail catheter, comprising a first lumen 42, a second lumen 44, and a third lumen 46. In this embodiment, the first lumen 42 is disposed around the circumference of the catheter 16 and the second and third lumens 44, 46 are disposed centrally within the interior 34. The second and third lumens 44, 46 are wholly surrounded by the first lumen 42. While this specific configuration is shown with respect to FIG. 1B, it will be appreciated that the interior 34 may comprise any number of lumens and the lumens can be arranged in any configuration.

The multiple lumens enable the catheter 16 to perform multiple functions without withdrawing the catheter 16 from the body or employing more than one device. For example, a plurality of openings 36 configured to aspirate a tissue may be in communication with the first lumen 42, a single opening 36 configured to receive the guidewire 18 therethrough may be in communication with the second lumen 44, and a plurality of openings 36 configured to deliver a substance to a tissue may be in communication with the third lumen 46. In this manner, the catheter 16 is capable of various functionalities including, without limitation, delivering suction to the cavity of the LAA, advancing the guidewire 18 to ensure accurate navigation throughout the body, and applying an adhesive to the LAA. It will be recognized that the catheter 16 may further comprise any combination of the aforementioned embodiments on a single device. In addition, the number of openings 36 located on the distal end 32 of the catheter 16 depend on the desired functionality of the occlusion assembly 10, and it will be understood that any number of openings 36 may be employed.

Figure 2A:
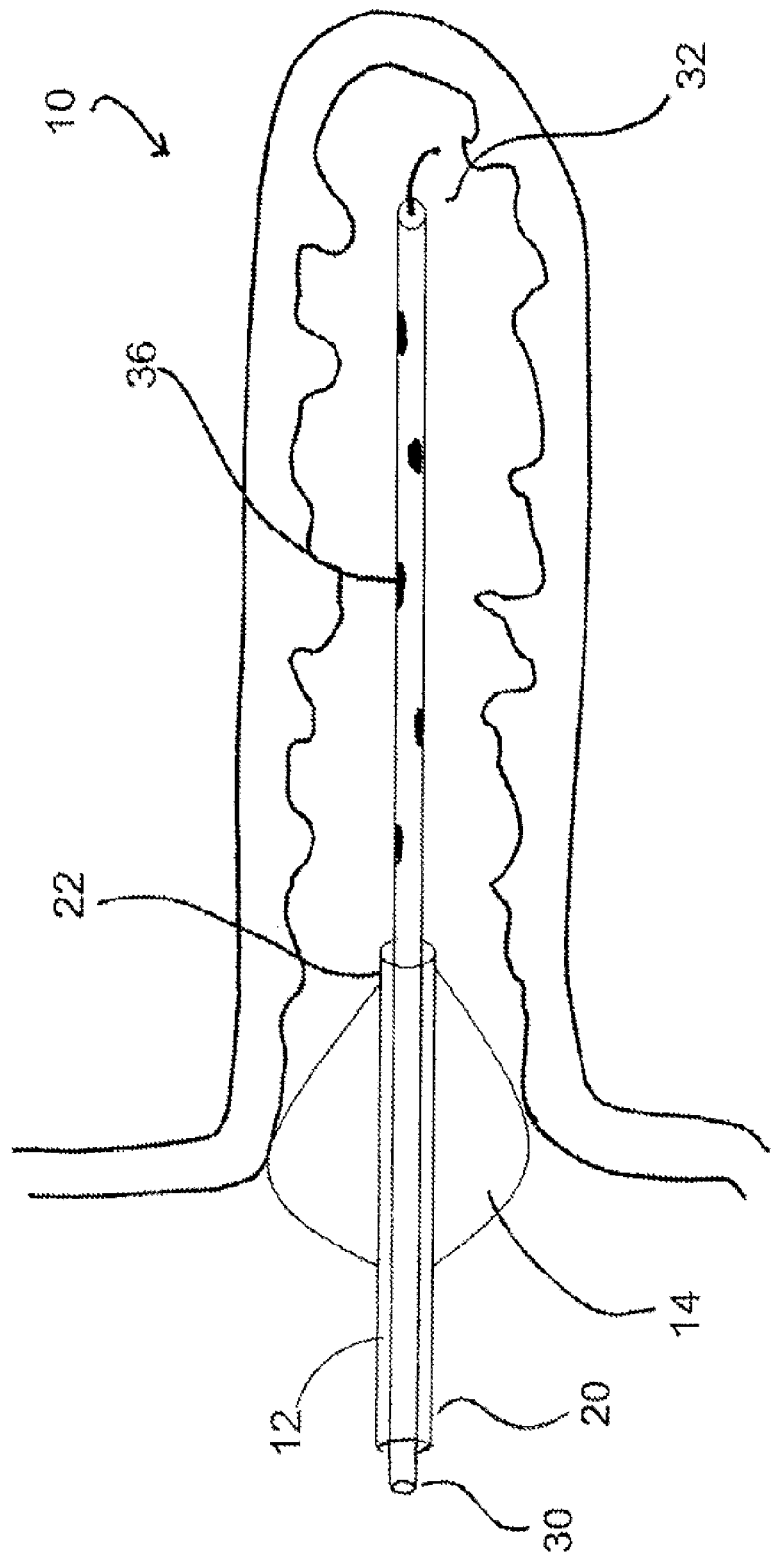

The operation of the occlusion assembly 10 will now be described with respect to the at least one embodiment of the catheter 16 shown in FIG. 2A. While this embodiment is described herein, it is understood that any of the embodiments of the catheters 16 described herein may be used to occlude a LAA.

Figure 2B:
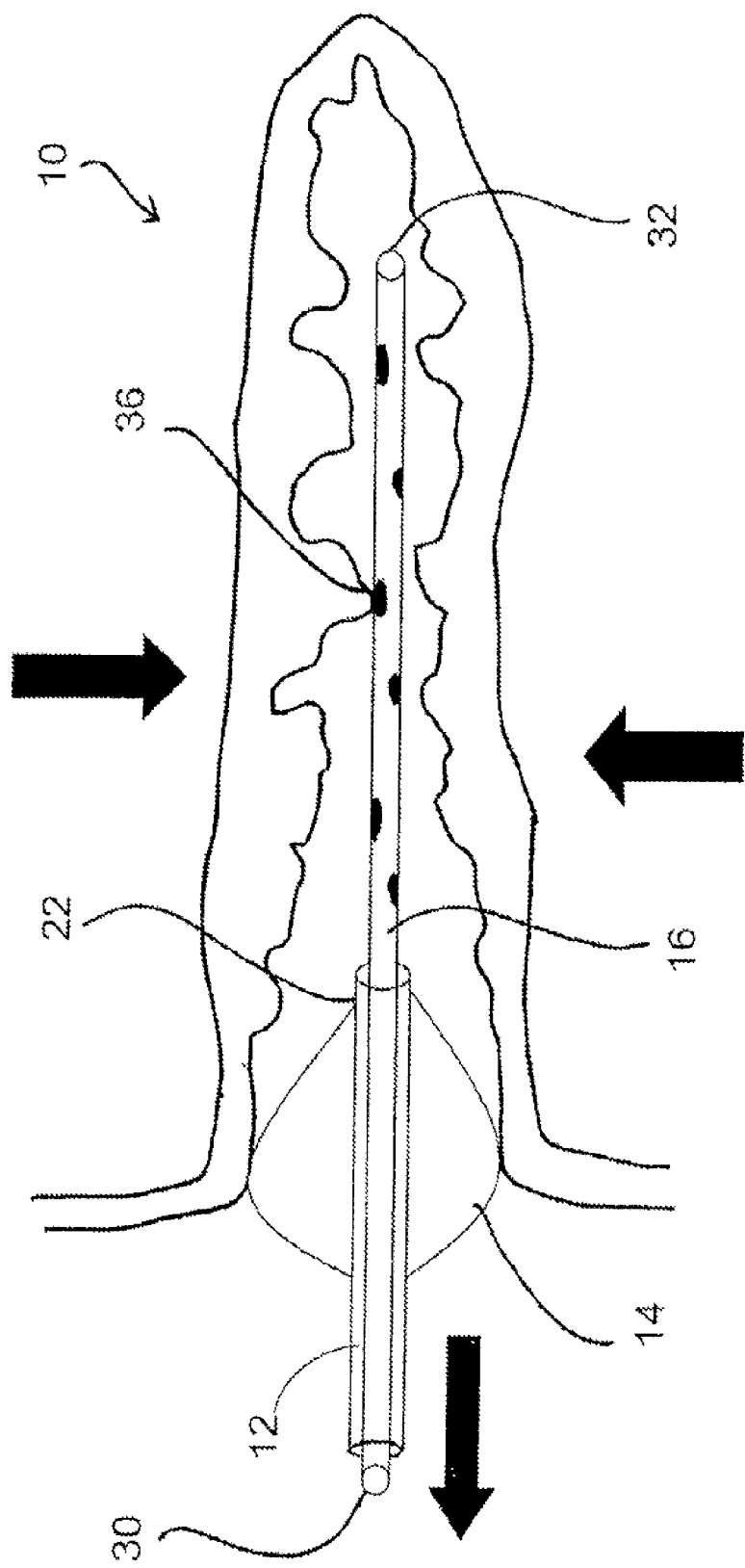

In operation, the guidewire 18 is threaded through the previously deployed shaft 12 and inserted into the cavity of the LAA, visualized by fluoroscopy or transesophageal echocardiography. After the guidewire 18 has accessed the cavity of the LAA, the distal end 32 of the catheter 16 is advanced through the distal end 22 of the shaft 12 and into the cavity of the LAA as shown in FIG. 2A. While maintaining the inflation of the balloon 14 occluding the LAA ostium, suction is initiated through the catheter 16. Specifically, a vacuum source is coupled with the first lumen 41 such that a vacuum is created therein. In this manner, the plurality of openings 36 function to aspirate the cavity of the LAA. This suctional force is maintained until a small amount of blood is removed from the LAA cavity and the LAA wall collapses as shown in FIG. 2B. After the LAA wall is completely collapsed, the suction is ceased. As the balloon 14 is occluding the LAA ostium and the LAA cavity is sealed, the collapse is maintained even in the absence of aspiration.

At this point, the catheter 16 is used to inject an adhesive 47 into the collapsed LAA cavity. In one embodiment the adhesive 47 comprises a biologic glue, however, the adhesive 47 can comprise any adhesive known in the medical arts. Accordingly, the occlusion assembly 10 may further comprise a delivery apparatus (not shown) for providing the adhesive 47 to the catheter 16. In one embodiment, the delivery apparatus is coupled with the third lumen 46 such that the adhesive 47 is advanced therethrough and applied to the cavity of the LAA through the at least one of opening 36 in communication therewith.

Figure 2C:
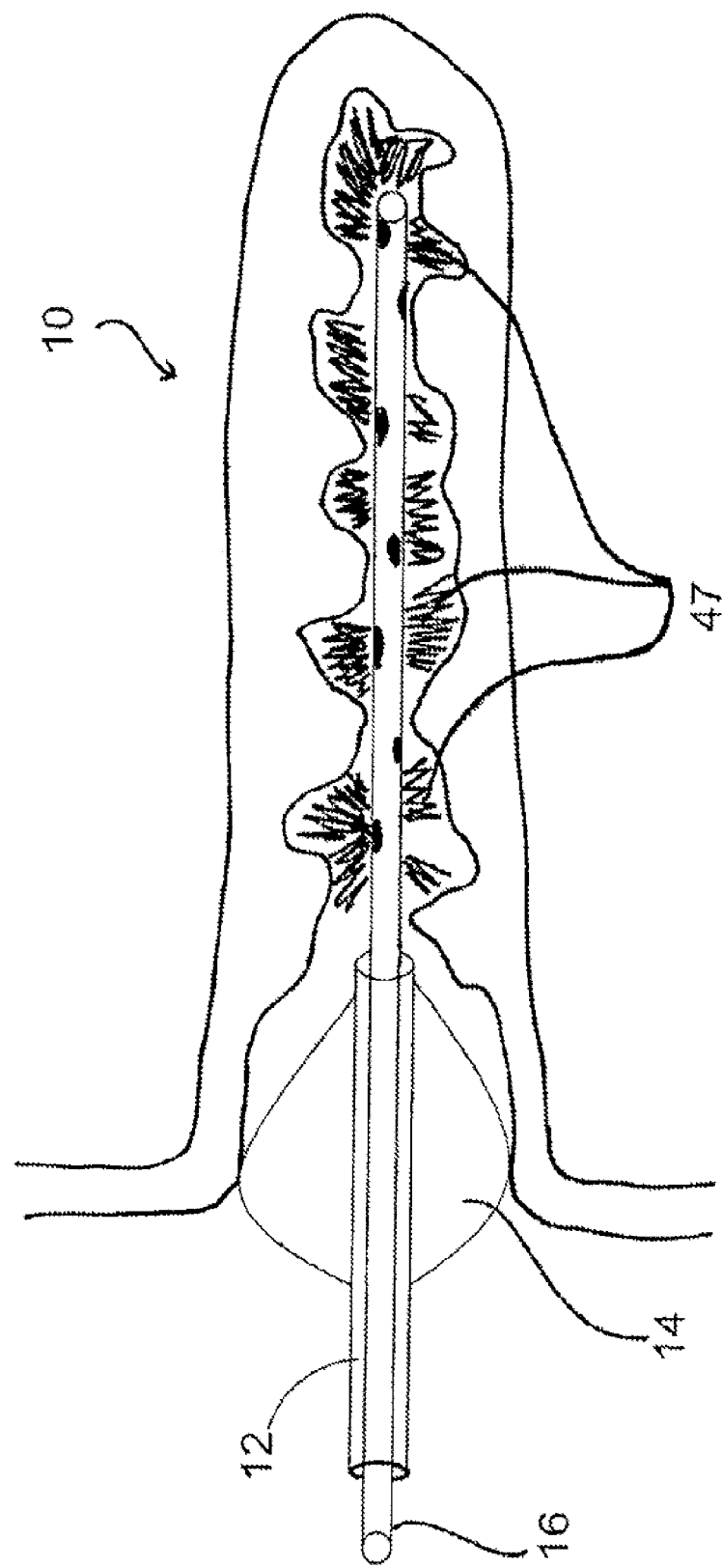
Figure 2E:
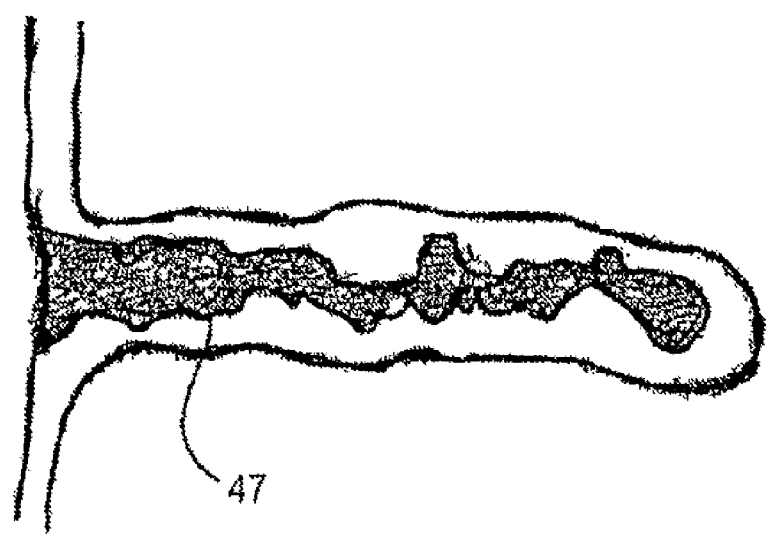

As shown in FIG. 2C, the application of the adhesive 47 within the collapsed LAA functions to seal the LAA. Further, as the catheter 16 delivers the adhesive 47 into the LAA cavity, the catheter 16 is slowly withdrawn through the interior 24 of the shaft 12 (FIG. 2D). After the adhesive 47 has completed sealing, the balloon 14 is deflated. Thereafter, the left atrium of the heart can be injected with dye in order to show angiographically the LAA occlusion. Once the success of the procedure has been confirmed, the shaft 12 and the balloon 14 are withdrawn from the body, across the interatrial septum and back through the femoral vein, thereby leaving the cavity of LAA sealed as shown in FIG. 2E.

Figure 3A:
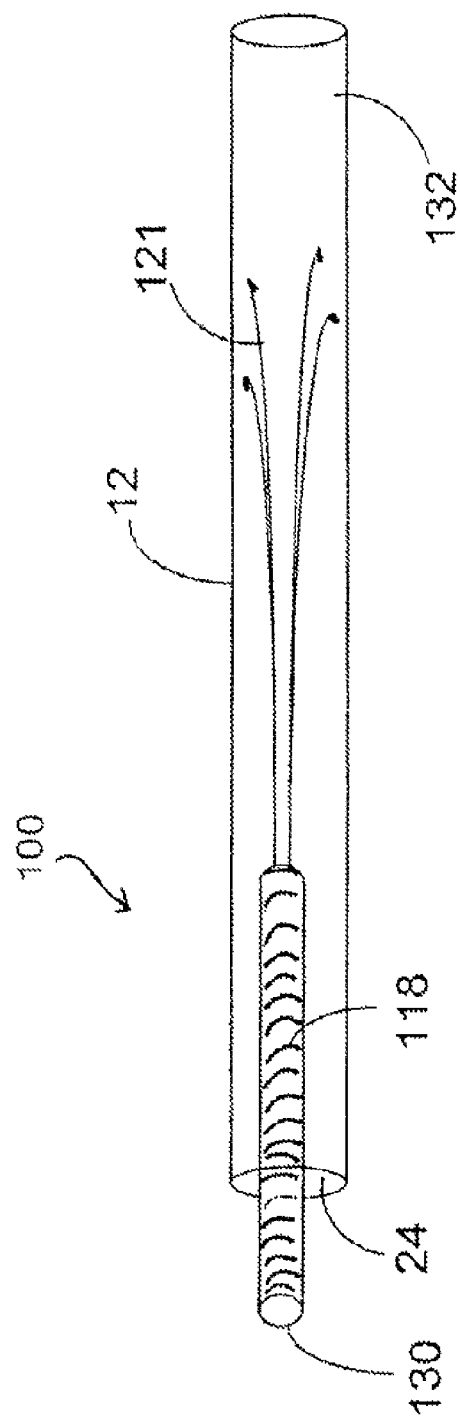
FIG. 3A shows a side view of at least one embodiment of an occlusion assembly.
Figure 3B:
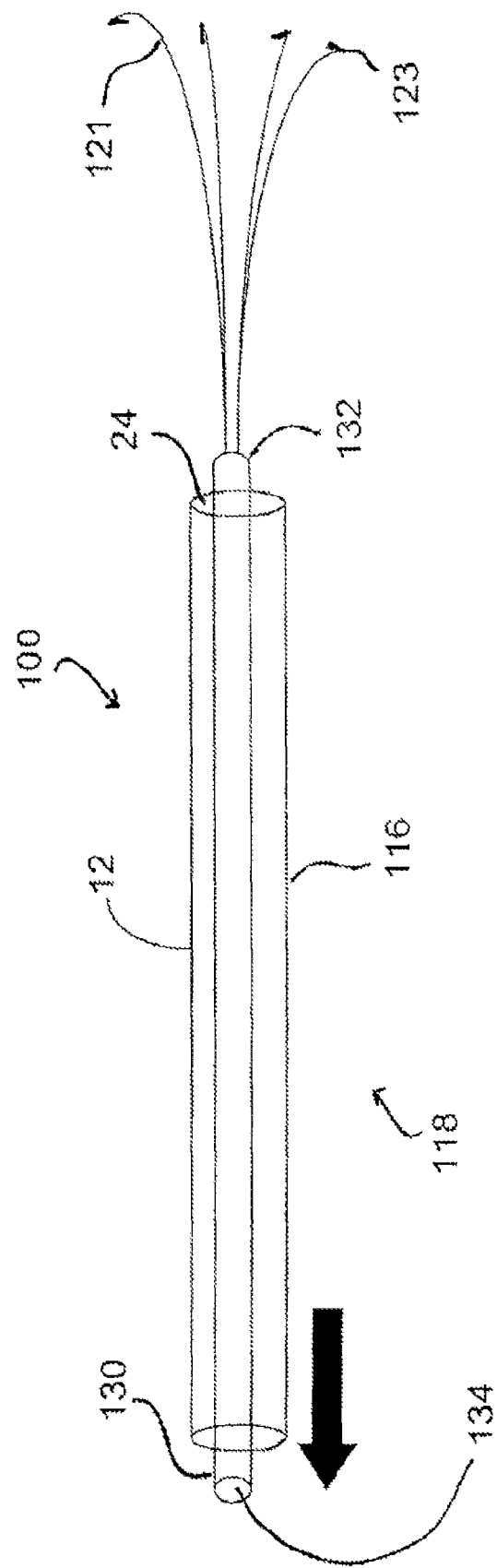
Figure 3C:
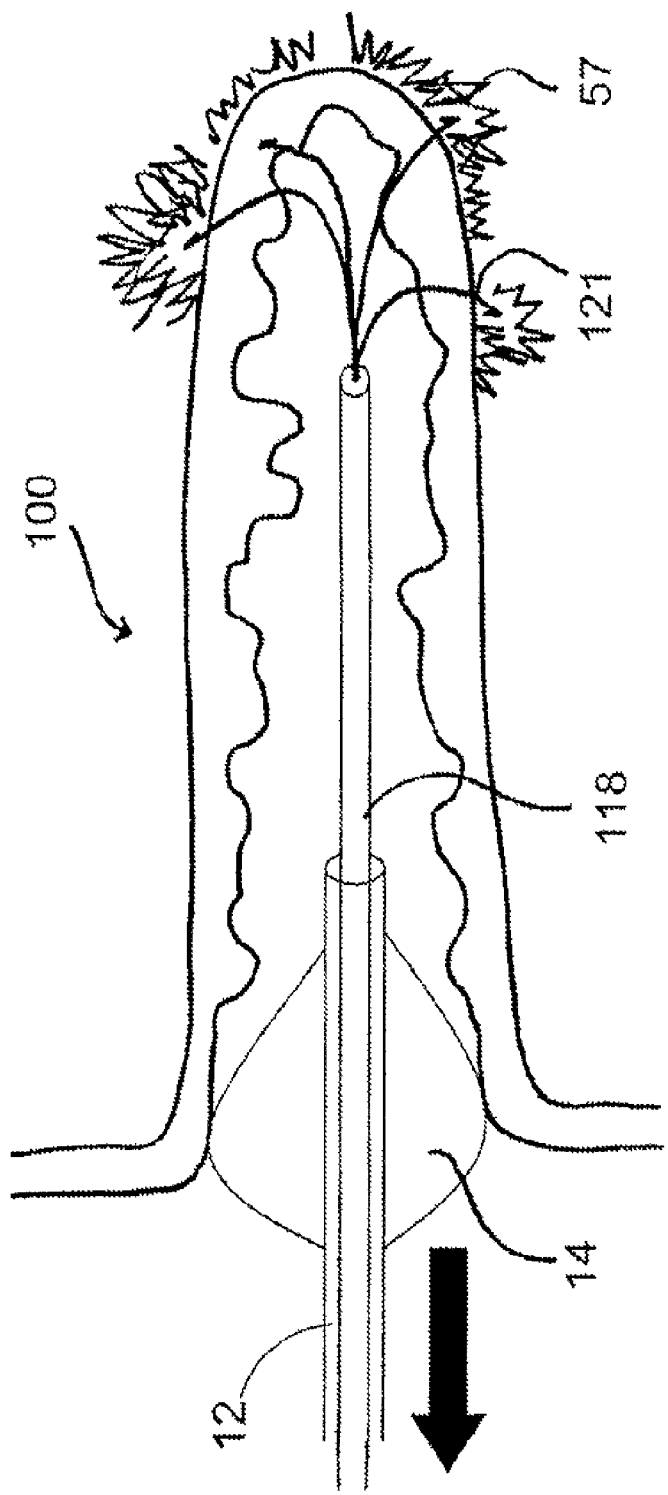

Now referring to FIG. 3C, an additional embodiment of an occlusion assembly 100 is shown. The occlusion assembly 100 comprises the shaft 12 and the balloon 14, and a catheter needle 118. The shaft 12 and the balloon 14 are configured identically to the shaft 12 and the balloon 14 of the occlusion assembly 10. Accordingly, configuration of the shaft 12 and the balloon 14 will not be described in detail with respect to the occlusion assembly 100, and like reference numerals between FIGS. 1A-2E and FIGS. 3A-3D will refer to like components.

As shown in FIG. 3B, the catheter needle 118 of the occlusion assembly 100 comprises a catheter 116 comprising a proximal end 130, a distal end 132, a hollow interior 134, and one or more needle wires 121. The catheter 116 may be composed of any material known in the medical arts suitable for application within the heart. The hollow interior 134 of the catheter 116 extends the length of the catheter 116, and in one embodiment, the interior 134 of the catheter 116 comprises at least two independent lumens.

The needle wires 121 are coupled with the distal end 132 of the catheter 116 and extend therefrom. The needle wires 121 are hollow so that a magnetic glue-like substance or other suitable substance (not shown) can pass therethrough. In one embodiment, each of the needle wires 121 comprise a lumen extending the length of the needle wire 121 and a distal needle aperture 123 in communication with the lumen. The needle wires 121 may be composed of any suitable material commonly used in the medical arts that serves the functions noted herein including, without limitation, a metallic compound. In one embodiment, the needle wires 121 are comprised of a very fine, hollow wire.

The catheter needle 118 can be slidably positioned within the interior 24 of the shaft 12. When the needle wires 121 of the catheter needle 118 are encased within the interior 24 of the shaft 12, the needle wires 121 are necessarily in a closed, joined form. In this manner, a clinician can effectively manipulate the catheter needle 118 containing the needle wires 121 in and around a patient's body without the needle wires 121 protruding and contacting surrounding tissue. However, once the catheter needle 118 is properly positioned (e.g., within the atrial appendage), a clinician may advance the catheter needle 118 through the distal end 22 of the shaft 12, thereby exposing the needle wires 121 and allowing them to expand as shown in FIG. 3B.

The lumen of each of the needle wires 121 is in communication with the hollow interior 134 of the catheter 116. In the embodiment where the catheter 116 comprises at least two independent lumens, the lumens of each of the needle wires 121 may be in communication with one of the lumens of the catheter 116, some of the lumens of the catheter 116, or all of the lumens of the catheter 116. In one embodiment, the lumen of each needle wire 121 is in communication with each of the lumens of the catheter 116. In this manner, a first lumen of the catheter 116 may provide a suctional force through the lumen of the needle wire 121, and a second lumen of the catheter 116 may provide delivery of an adhesive or medicament through the lumen of the needle wire 121. Alternatively, and in the same manner, a first lumen of the catheter 116 may provide a first adhesive to the needle wire 121 and a second lumen of the catheter 116 may provide a second adhesive to the needle wire 121.

As previously described, the needle wires 121 comprise a distal aperture 123. The distal aperture 123 is in communication with the lumen of the needle wire 118, and as such, in communication with the interior 134 of the catheter 116. In this manner a magnetic glue-like substance can be advanced through the interior of the catheter 116, into the lumen of the needle wire 118, and delivered to a targeted tissue through the needle aperture 123. Alternatively, a suctional force can be transmitted through the needle aperture 123. In one embodiment, the needle wires 121 are connected to an injection apparatus (not shown) for glue delivery via the hollow interiors of the needle wires 121, and a vacuum source (not shown) to supply the requisite suction necessary to aspirate the LAA cavity.

The needle wires 121 may further have an expanded memory. For example, the needle wires 121 may be initially closed and then expanded once exposed to a particular temperature or other stimuli. In other words, the needle wires 121 may comprise an original configuration, which may include, without limitation, a bend and/or a curve in the needle wires 121. When the needle wires 121 exhibiting their original configuration are positioned within the shaft 12, the original configuration may be altered (e.g., the needle wires 121 may be straightened while positioned within the interior of the shaft 12). When the needle wires 121 are thereafter protracted from the distal end 22 of the shaft 12, the original configuration of the needle wires 121 may then present itself.

The occlusion assembly 100 may be used in conjunction with an injection apparatus and a magnetic glue-like substance capable of injection by the injection apparatus. The injection apparatus may comprise any device capable of advancing a magnetic glue-like substance into the needle wires 121. The magnetic glue-like substance may exert a sufficient magnetic force so that when the magnetic glue-like substance is positioned on the exterior wall of an atrial appendage, the magnetic glue-like substance functions to effectively collapse the structure of the atrial appendage. The magnetic glue-like substance can be composed of any commonly used adhesive substance known in the medical arts.

In operation, the occlusion assembly 100, the shaft 12 and balloon 14 are delivered and deployed as previously described. Specifically, the balloon 14 is inflated and positioned to collect occluding the ostium of the LAA. Thereafter, the catheter needle 118 is delivered through the interior 24 of the shaft 12 (see FIG. 3A) and suction of the LAA cavity is initiated. In one embodiment, the suction can be provided through the needle apertures 123 of the needle wires 121. In an alternative embodiment, a vacuum source can be applied directly to the proximal end 20 of the shaft 12. The suctional force of the vacuum is maintained and/or increased until an amount of blood is removed from the LAA cavity and the LAA wall collapses. Even after the wall collapses, a degree of suction is maintained through the catheter 116 or the shaft 12 in order to ensure the balloon 14 maintains optimal position.

Under fluoroscopic and transesophageal echocardiography control, the catheter needle 118 is advanced through the distal end 22 of the shaft 12 and the walls of the LAA are punctured with the needle wires 121 (see FIG. 3D). The needle wires 121 are capable of completely puncturing the LAA wall, such that the needle apertures 123 of the needle wires 121 are positioned within the pericardial sac. Due to the relatively thin nature of the needle wires 121, the puncture of the LAA wall has minimal effect on the pressure within the LAA cavity. However, in one embodiment, the suctional pressure may be slightly increased during this step to facilitate a constant pressure within the LAA cavity.

Figure 3E:
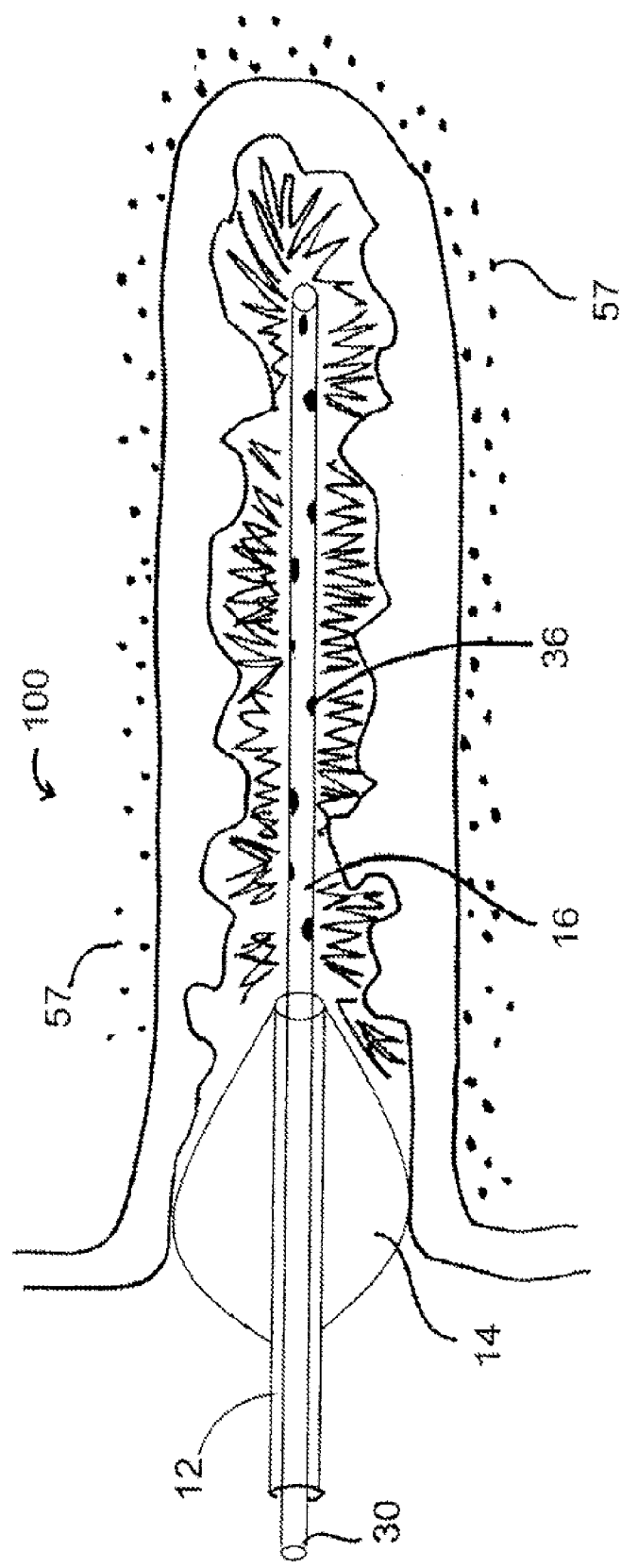
FIG. 3E shows a side view of at least one embodiment of an occlusion assembly as applied to treat a left atrial appendage.

While the needle apertures 123 are positioned within the pericardial sac, an amount of magnetite microbeads 57 are delivered through the needle apertures 123 of the needle wires 121 onto the epicardial surface. In one embodiment, this delivery is achieved through the use of the injection apparatus previously described. The magnetite microbeads 57 may be delivered as an adhesive solution, a powder, or as carbon dioxide spray. As shown in FIG. 3D, after the first application is complete, the needle wires 121 are used to puncture the LAA and deliver the microbeads 57 to the epicardial surface in multiple locations. Once a sufficient amount of magnetite microbeads 57 have been applied to the external surface of the atrial appendage, the needle catheter 118 may be withdrawn through the shaft 12 and removed from the body. Alternatively, prior to being withdrawn, the needle catheter 118 may deposit an amount of magnetite microbeads 57 within the interior of the LAA cavity such that the magnetite microbeads 57 are distributed between the LAA wall trabecules (pectinate muscles). The catheter 16 (as shown in FIGS. 1A-1E) is thereafter introduced into the LAA cavity and an adhesive biological glue is injected therein to achieve an adequate seal of the LAA ostium (see FIG. 3E).

Figure 3F:
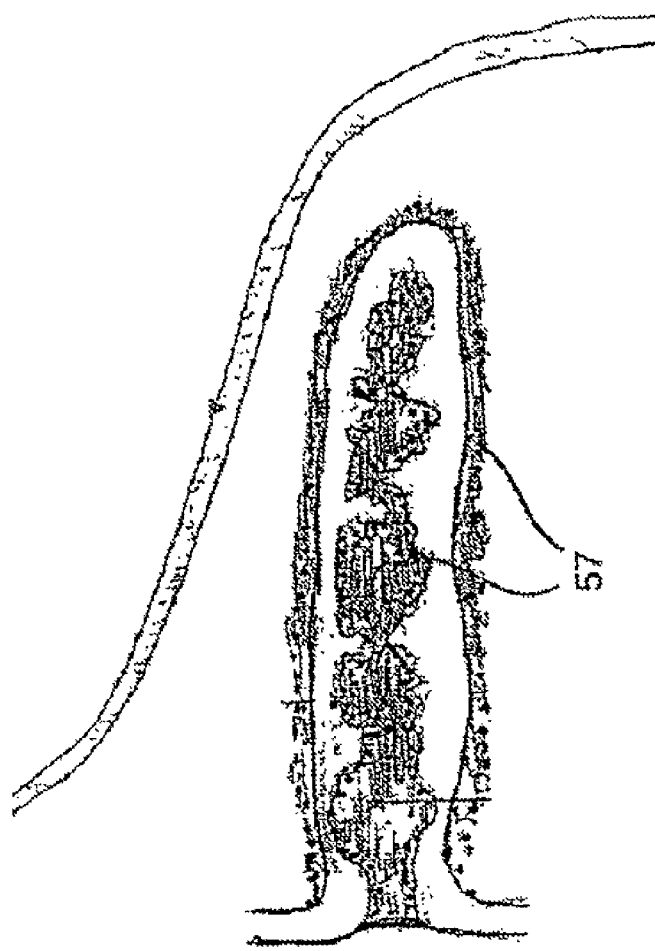
FIG. 3F shows a side view of a left atrial appendage that has been occluded using the occlusion assembly of FIGS. 3A-E.

The inflation of the balloon 14 is maintained during the requisite sealing time and the catheter 16 is withdrawn from the body through the shaft 12. The magnetic attraction between the magnetite microbeads 57 on the epicardial surface of the LAA and the magnetite microbeads 57 disposed within the interior of the LAA functions to create a constricted and tightened LAA, thereby promoting the occlusion of the LAA (see FIG. 3F).

Figure 4A:
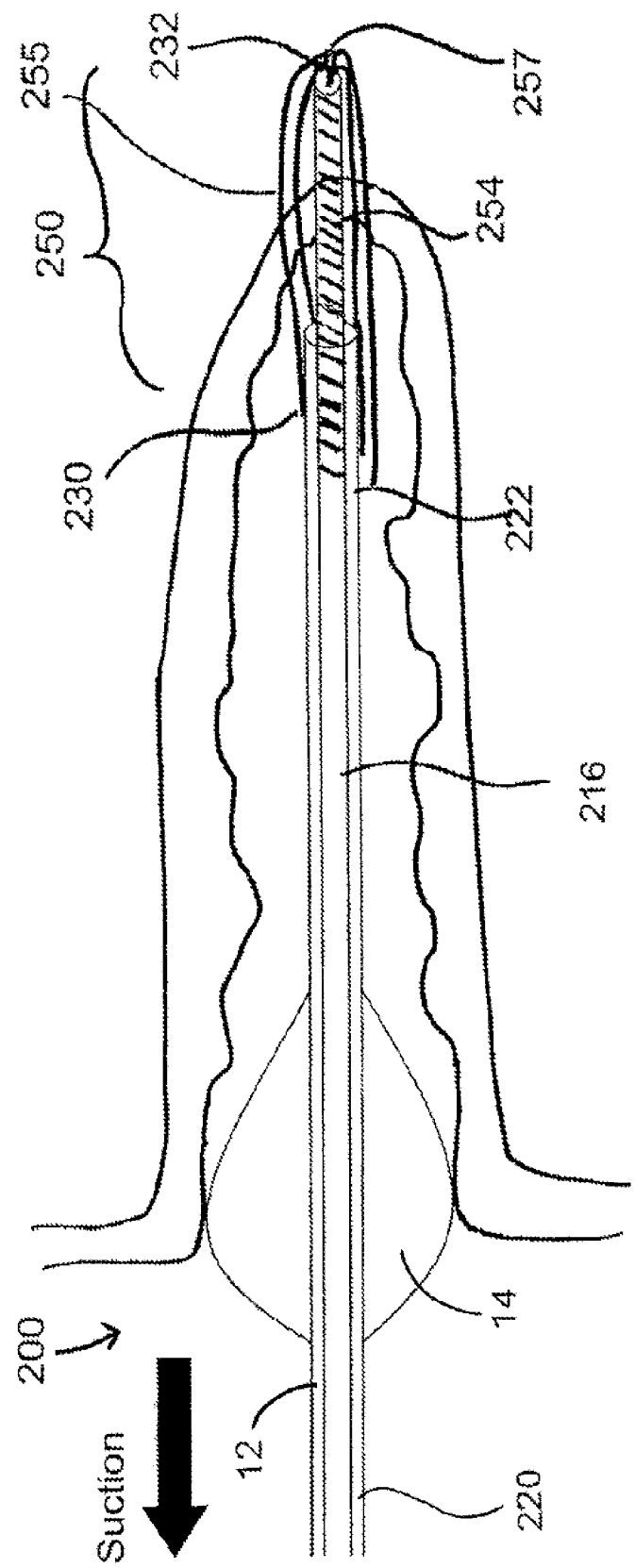
FIGS. 4A-4B show two side views of at least one embodiment of an occlusion assembly as applied to treat a left atrial appendage.
Figure 4B:
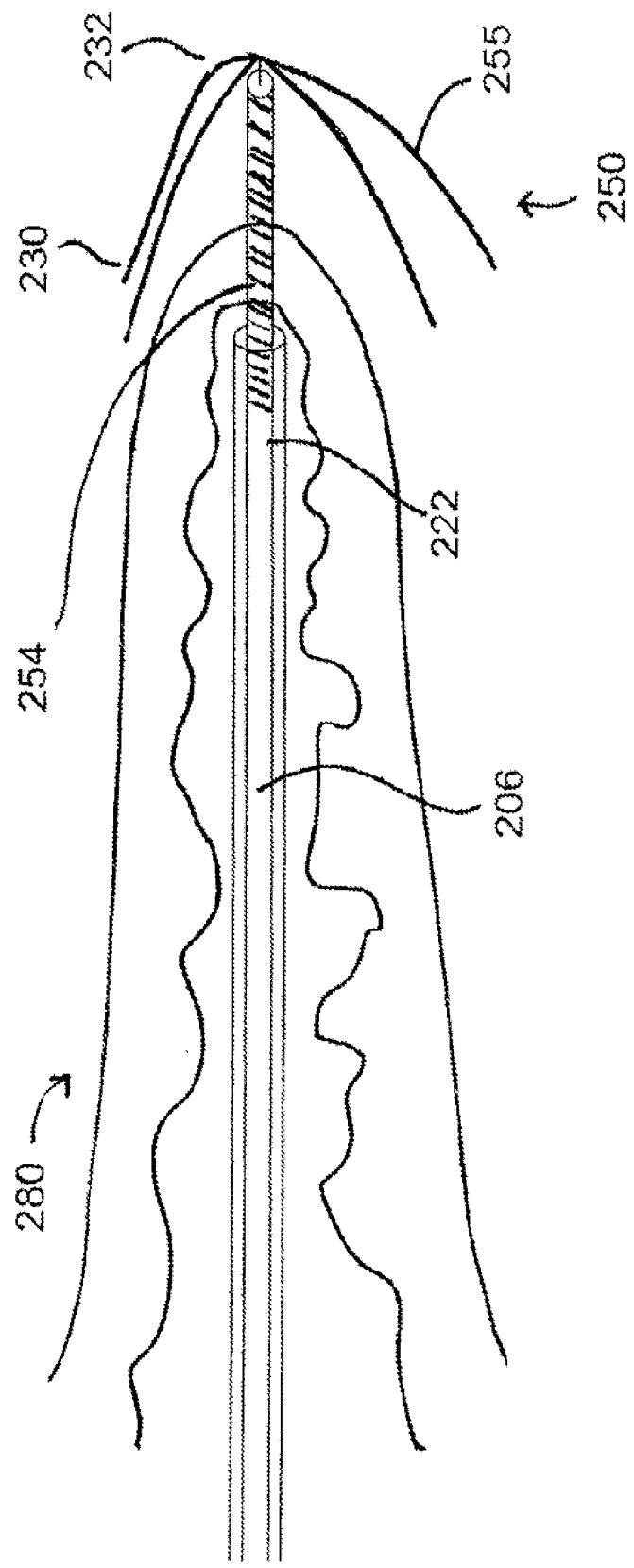

Now referring to FIGS. 4A and 4B, another embodiment of an occlusion assembly 200 is shown. The occlusion assembly 200 comprises the shaft 12 and the balloon 14, and a catheter 216. The shaft 12 and the balloon 14 are configured identically to the shaft 12 and the balloon 14 of the occlusion assembly 10. Accordingly, configuration of the shaft 12 and the balloon 14 will not be described in detail with respect to the occlusion assembly 200, and like reference numerals between FIGS. 1A-2E and FIGS. 4A-4B will refer to like components.

In one embodiment, a catheter 216 is used in conjunction with the shaft 12 and the balloon 14 to collapse an atrial appendage. The catheter 216 comprises a proximal end 220, a distal end 222, and a clip assembly 250 extending from the distal end 222 of the catheter 216. The clip assembly 250 comprises a magnetic bar 254 and a plurality of ferromagnetic clips 255 positioned in an umbrella-like configuration. The magnetic bar 254 is removably coupled with the distal end 222 of the catheter 216 such that once the clip assembly 250 is anchored to a tissue, the catheter 216 can be removed therefrom and withdrawn from the body. Further, in at least one embodiment, the magnetic bar 254 initially comprises a sheath disposed thereon to prevent any magnetic attraction between the ferromagnetic clips 255 and the magnetic bar 254 prior to deployment of the device.

Each of the ferromagnetic clips 255 comprising the clip assembly 250 comprises a first end 230 and a second end 232. In addition, each of the ferromagnetic clips 255 exhibits a magnetic polarity. The second ends 232 of the ferromagnetic clips 255 are hingedly coupled with the magnetic bar 254, such that a hinged apex 257 is formed. From this hinged apex 257, the clip assembly 250 is capable of moving between a compressed position (closed umbrella) and an expanded position (open umbrella).

The ferromagnetic clips 255 are specifically arranged around the magnetic bar 254 such that a magnetic force is generated between the components of the clip assembly 250. However, for as long as the sheath is disposed on the magnetic bar 254, the various components of the clip assembly 250 may be easily maneuvered.

When the clip assembly 250 is positioned in a compressed position, each of the ferromagnetic clips 255 lay substantially parallel with the catheter 116 (see FIG. 4A). In addition, the apex 257 of the clip assembly 250 comprises a needle-like surface that is capable of puncturing a targeted tissue. When the ferromagnetic clips 255 are positioned in the expanded position, the first ends 230 of the clips 255 extend radially from the magnetic bar 257 such that the ferromagnetic clips 255 are positioned in the expanded position (see FIG. 4B).

The umbrella-like configuration of the clip assembly 250 enables the clip assembly 250 to puncture a targeted tissue and subsequently anchor thereto. For example, when the ferromagnetic clips 255 are positioned in the compressed position, the apex 257 of the clip assembly 250 can be used to puncture the tissue of the LAA. Thereafter, the ferromagnetic clips 255 in the compressed position are advanced through the puncture hole and into the pericardial space. Once the first ends 230 of the ferromagnetic clips 255 clear the puncture hole in the tissue, the catheter 216 is withdrawn through a pull back technique. As the first ends 230 of the ferromagnetic clips 255 are not as tightly configured as are the second ends 232 which form a needle-like tip, the first ends 230 cannot retract through the puncture hole in the tissue. Accordingly, the first ends 230 of the ferromagnetic clips 255 expand radially away from the catheter 216 and into the expanded position.

Figure 5A:
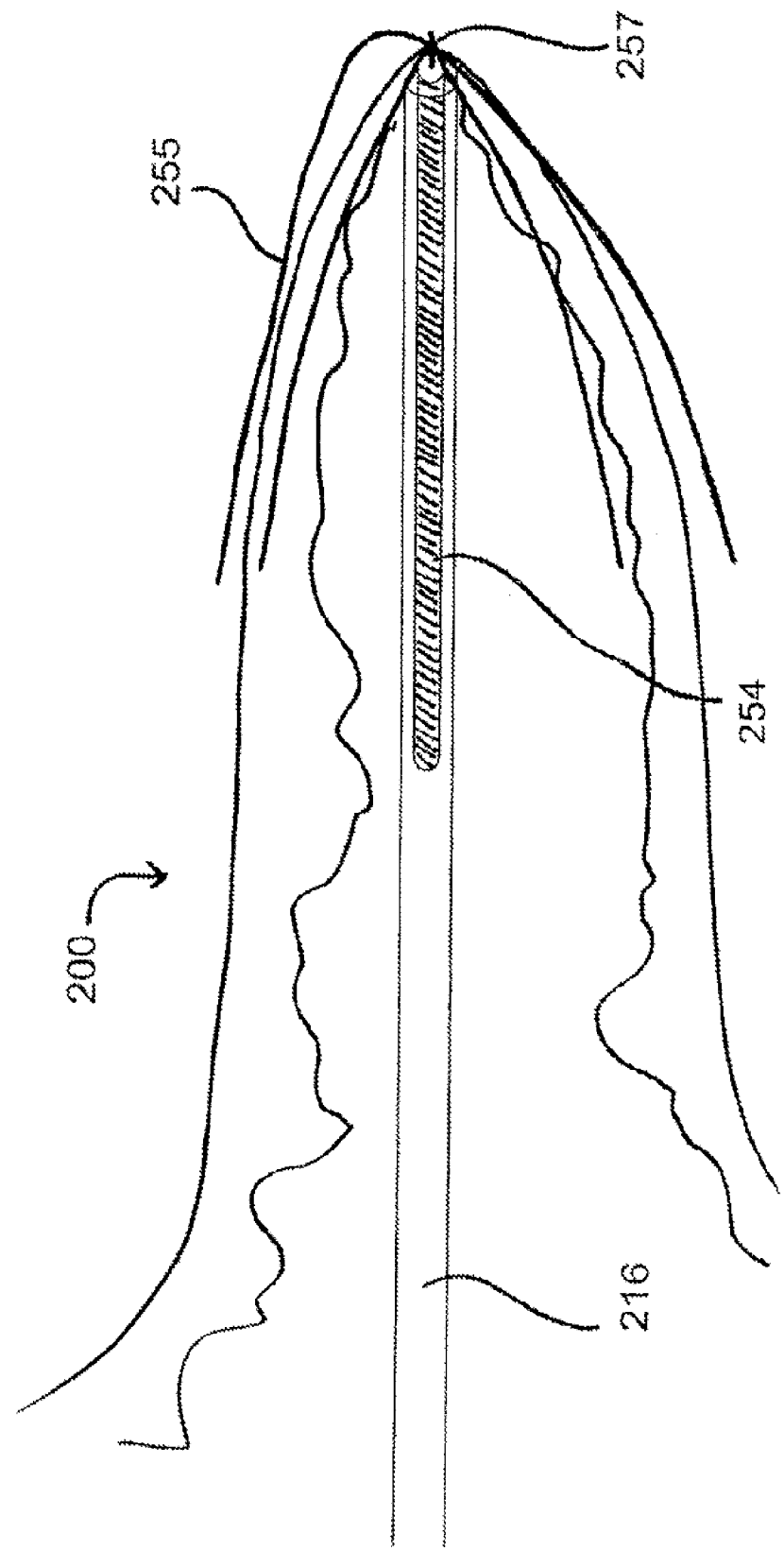
FIG. 5 shows side views of the occlusion assembly of FIGS. 4A-4B in operation.
Figure 5B:
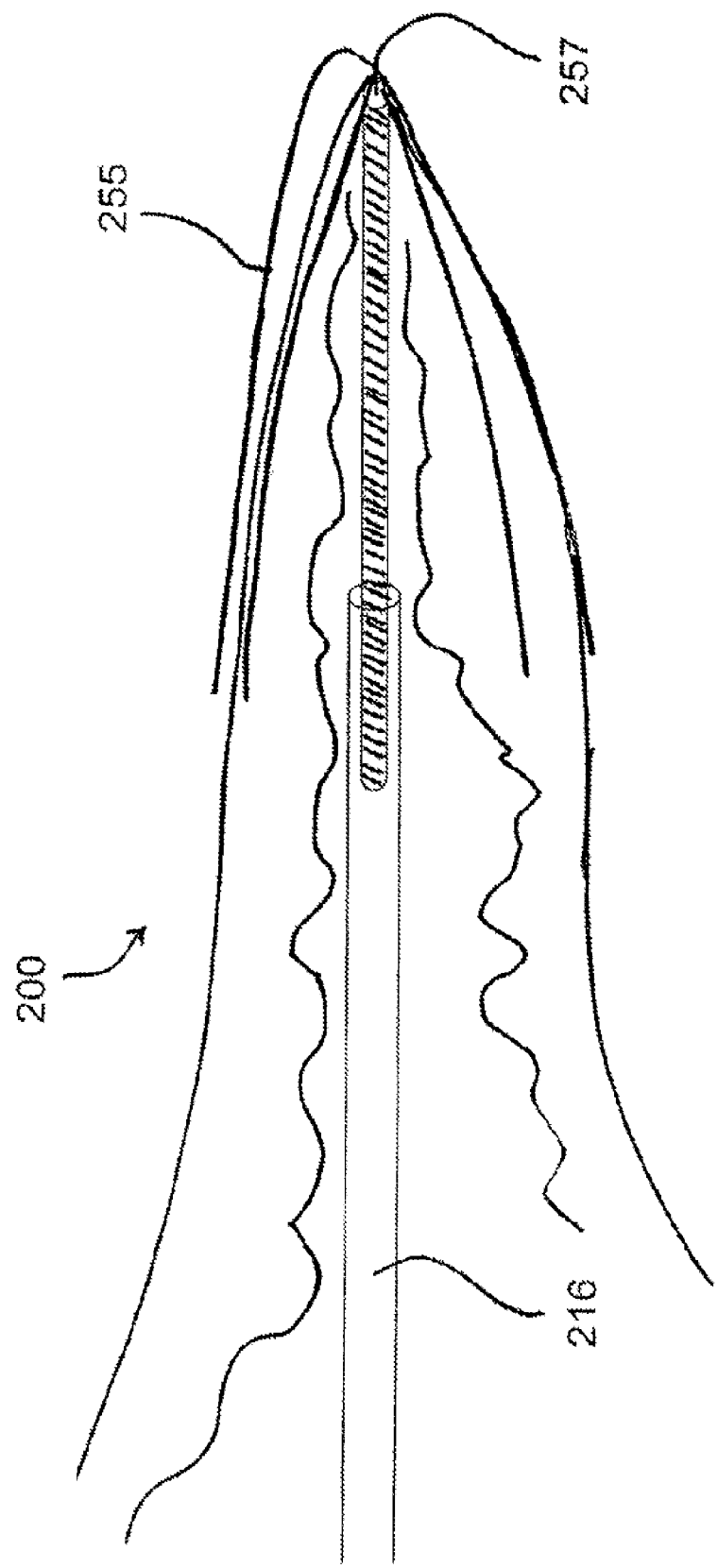
Figure 5C:
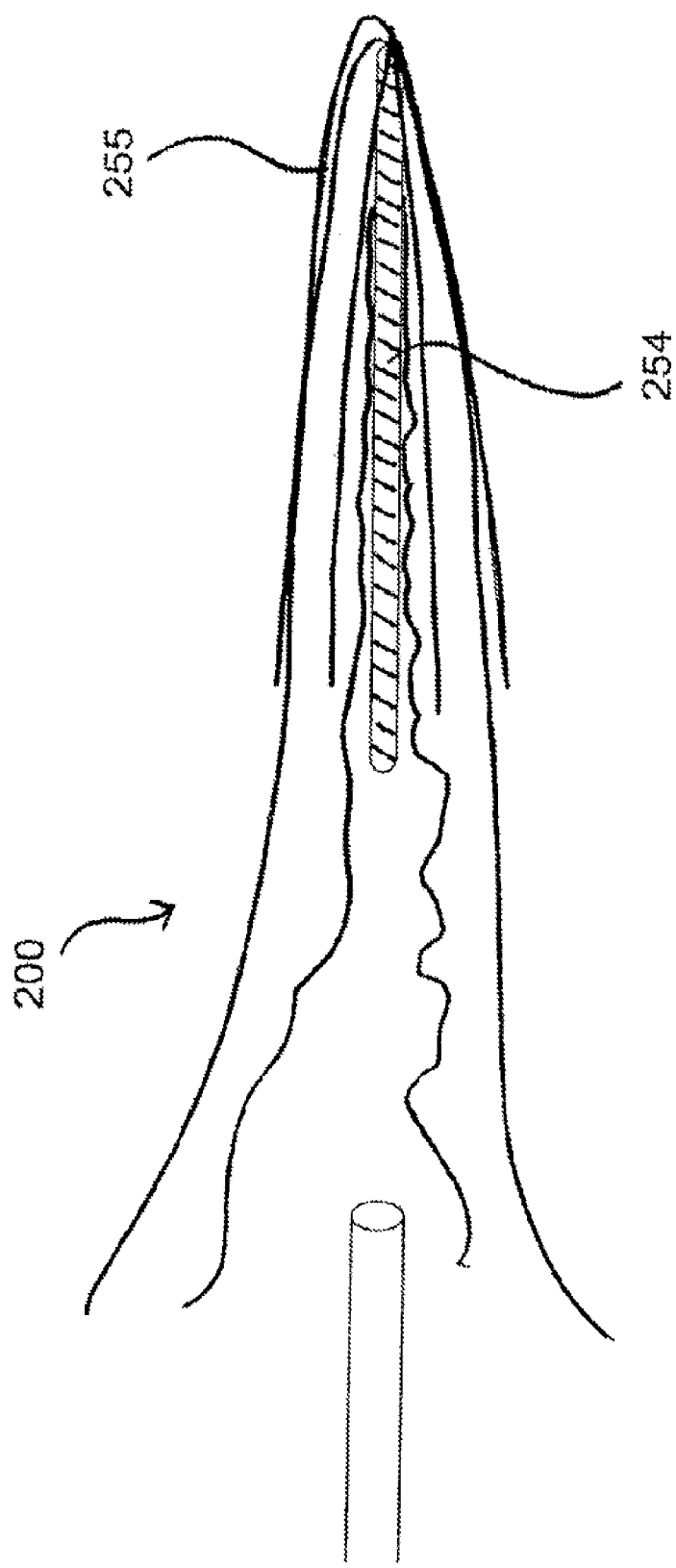

The magnetic bar 254 remains positioned within the interior of the LAA. At this point, the sheath disposed on the magnetic bar 254 to prevent magnetic interaction between the magnetic bar 257 and the ferromagnetic clips 255 is removed. Once the sheath is removed, the magnetic attraction between the components of the clip assembly 250 causes the ferromagnetic clips 255 to move into the compressed position, thereby applying pressure to the exterior of the LAA as shown in FIGS. 5A-5C. In this manner, a sandwich effect is created around the exterior of the LAA and the LAA cavity is caused to collapse. Once the desired collapse has been achieved, the catheter 216 may be uncoupled from the magnetic bar 257 (through unscrewing or some other means) and withdrawn from the body.

Figure 6A:
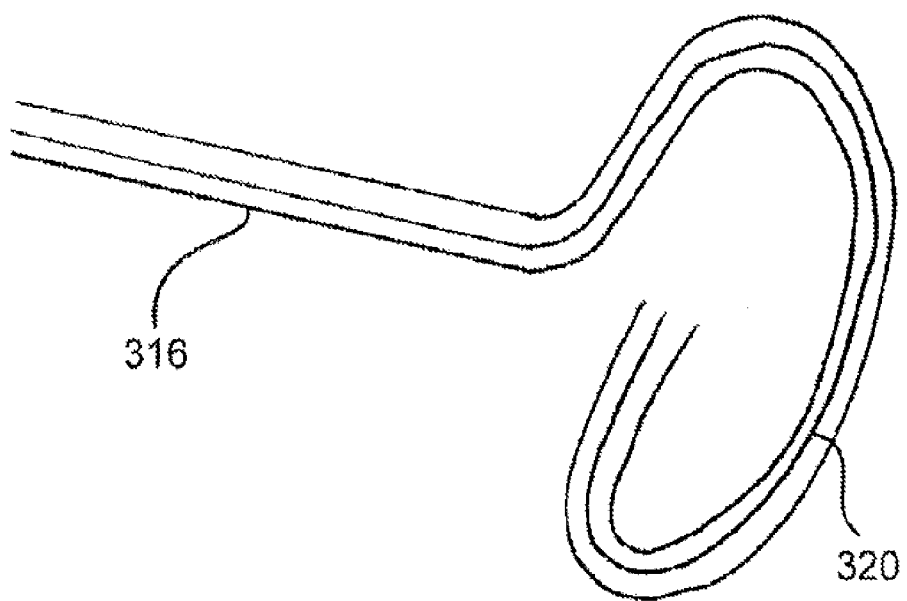
FIGS. 6A-6C show various embodiments of a pigtail catheter that may be used to treat a left atrial appendage.
Figure 6B:
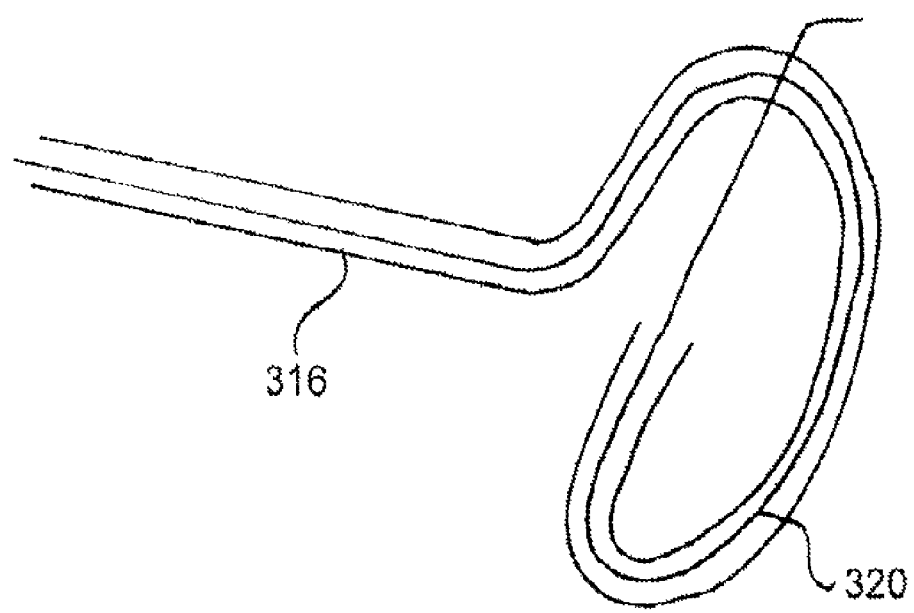
Figure 6C:
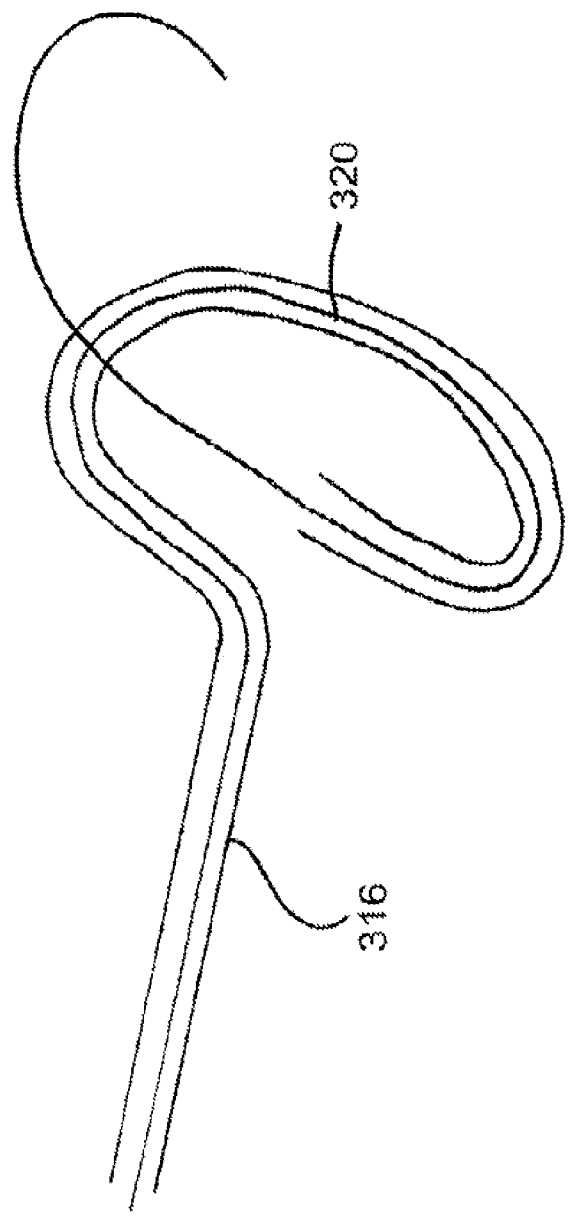
Figure 7:
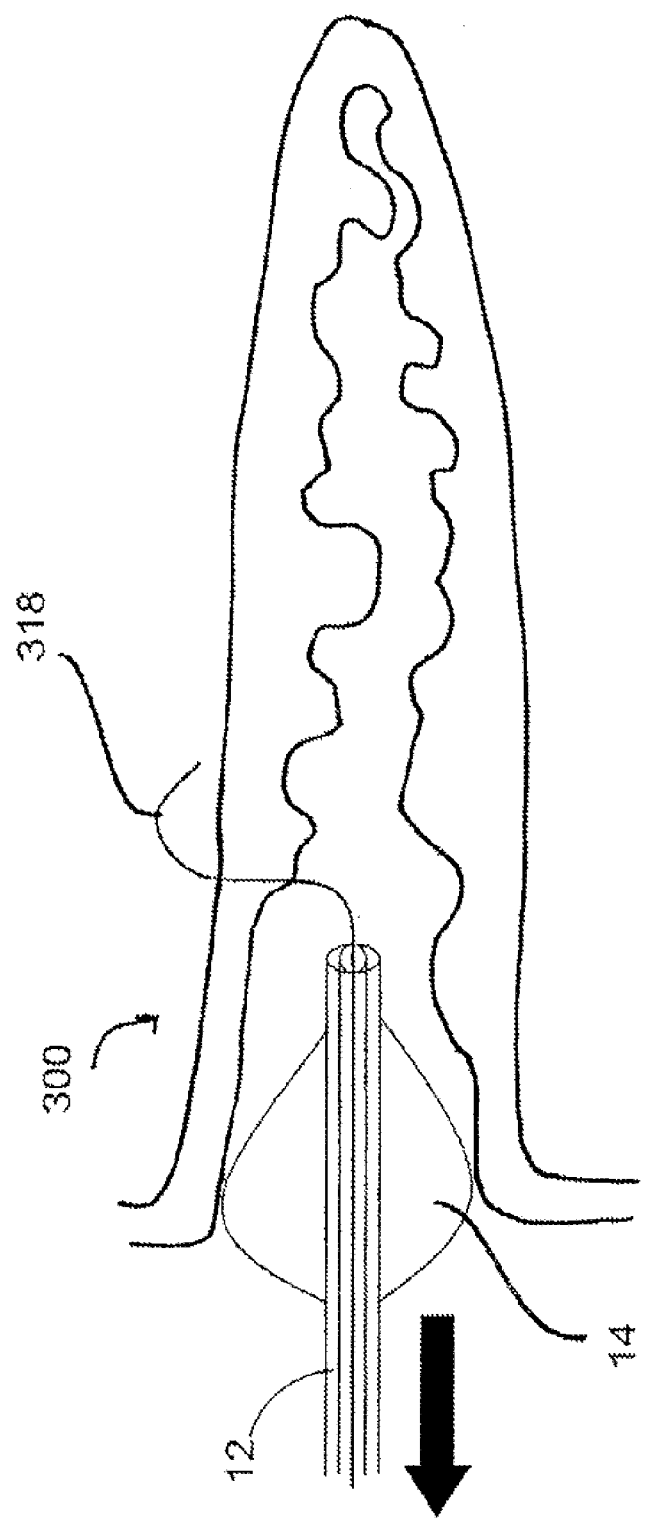
Figure 8:
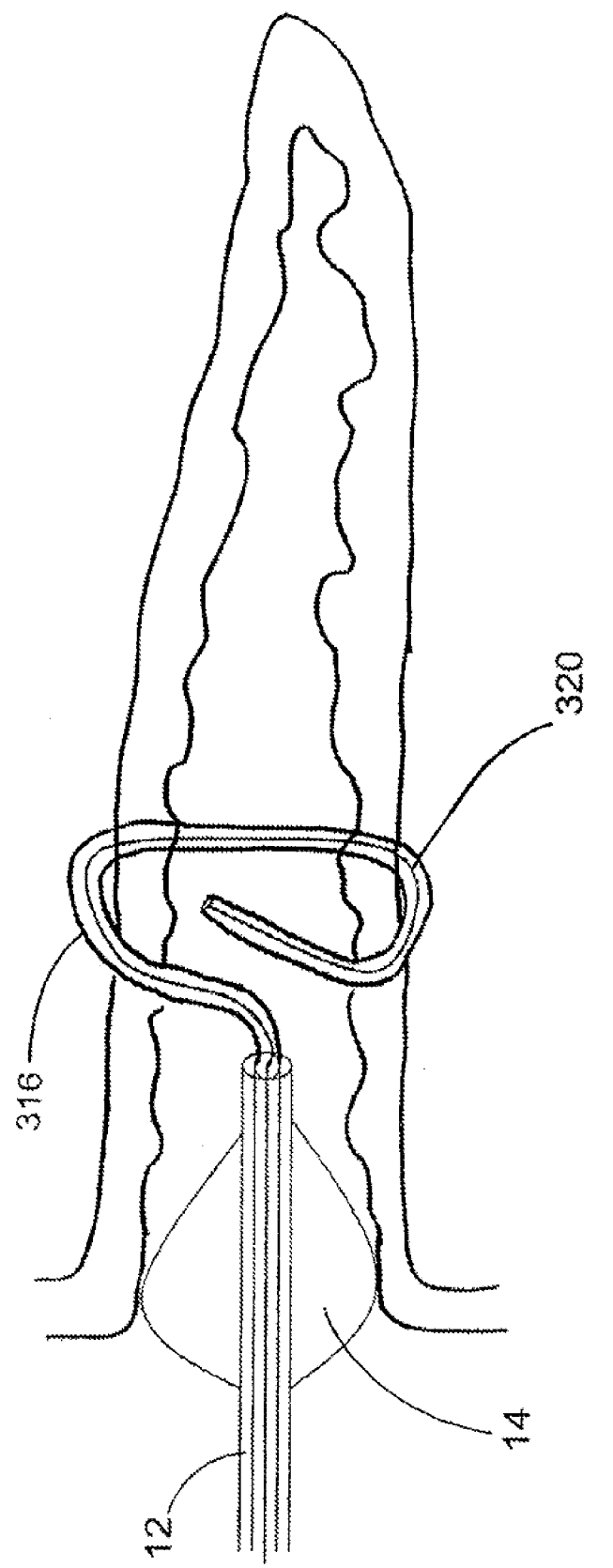
Figure 9B:
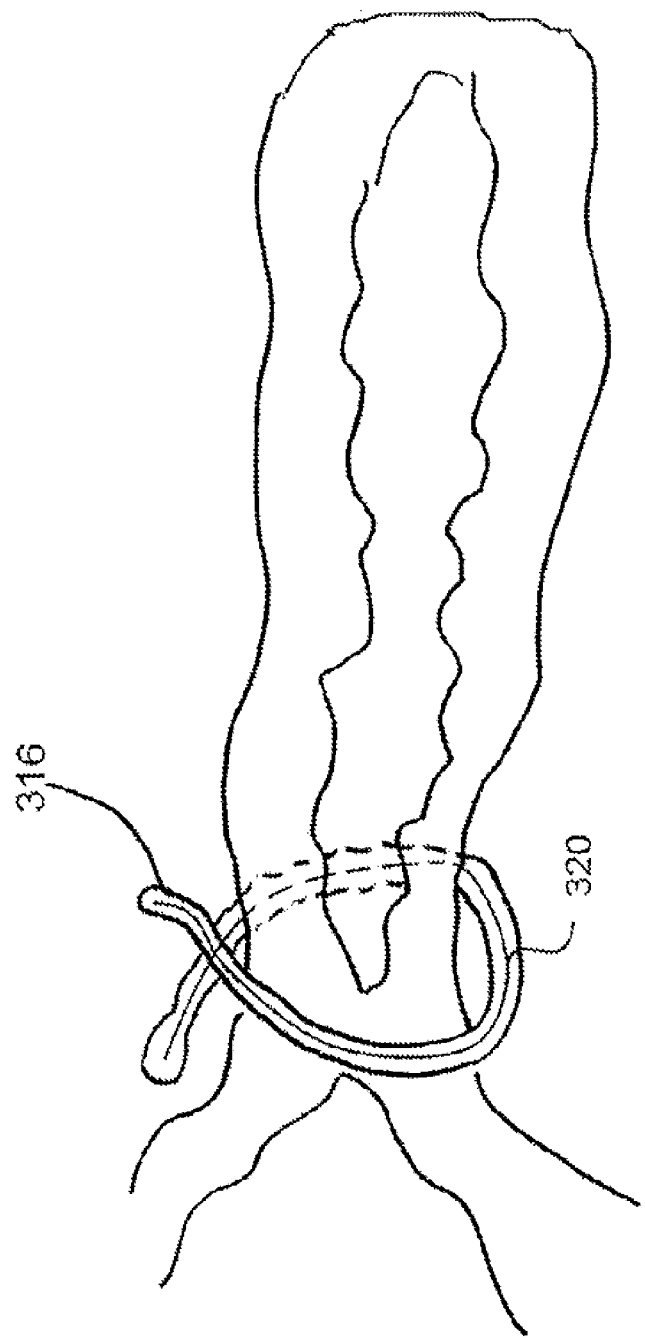

Now referring to FIGS. 6A-9B, at least one embodiment of an occlusion assembly 300 is shown. As shown in FIGS. 7 and 8, the occlusion assembly 300 comprises the shaft 12, the balloon 14, a catheter 316, a needle wire 318, and a memory wire 320. The shaft 12 and the balloon 14 are configured identically to the shaft 12 and the balloon 14 of the occlusion assembly 10. Accordingly, configuration of the shaft 12 and the balloon 14 will not be described in detail with respect to the occlusion assembly 300, and like reference numerals between FIGS. 1A-2E and FIGS. 6A-9B will refer to like components.

As shown in FIGS. 7 and 8, occlusion assembly 300 comprises a catheter 316, a needle wire 318, and a memory wire 320. The catheter 316 comprises a preformed pigtail catheter having a plurality of lumens. FIGS. 6A-6C illustrate various configurations of the catheter 316, although the catheter 316 may comprise any other configuration capable of advancing the memory wire 320 through the base of the LAA. In one embodiment, the catheter 316 comprises three lumens: a first lumen coupled with a vacuum device, a second lumen for receiving a guide wire, and a third lumen for receiving the memory wire 320 and the needle wire 318. The memory wire 320 may be made of a shape memory alloy, such as nitinol. Thus, the wire 320 is relatively straight when deployed through the catheter 316. However, after introduction into the body and placement around the atrial appendage, by manipulating the wire to wrap around the appendage, the wire forms the shape of a loop. In one embodiment, the memory wire 320 is relatively short and is employed with a separate wire guide to facilitate accurate placement.

The catheter 316 is delivered into the LAA and suction is applied thereto as previously described herein. The needle wire 318 is advanced through the shaft 12, and is used to puncture the base of the LAA, as shown in FIG. 7. After the LAA wall is punctured, the atraumatic guide wire 18 is introduced into the puncture hole and advanced through the LAA wall and into the pericardial space. Once the puncture hole is maintained by the guide wire 18, the needle wire 318 is withdrawn back into the LAA and thereafter removed from the body.

The catheter 316 is then advanced, following the guide wire 18, through the puncture in the LAA wall. Further, the pigtail configuration of the catheter 316 is utilized to wrap around the base of the LAA, as shown in FIG. 8. At this point, the guide wire 18 is withdrawn and removed, and the wire guide is advanced in its place. The wire guide functions to push and deliver the short memory wire 320 to the base of the LAA. Accordingly, the wire guide effects the placement of the memory wire 320 through pushing and pulling the memory wire 320 around the base of the LAA as shown in FIG. 9A. In this manner, the two ends of the memory wire 320 are crossed around the base of the LAA. Concurrent with the manipulation of the memory wire 320, the catheter 316 is slowly withdrawn from the LAA cavity through the shaft 12. Due to the shape memory alloy properties of the memory wire 320 and its placement around the base of the LAA, the memory wire 320 effectively occludes the LAA without the use of adhesives or sutures.

Figure 10:
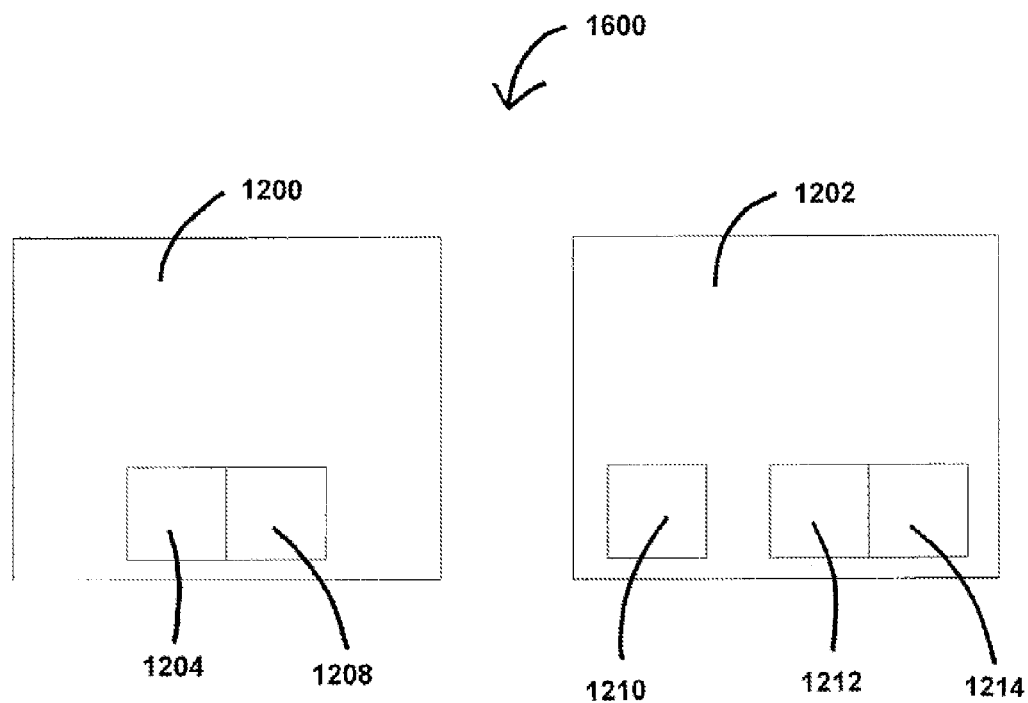
FIG. 10 shows a diagram of the components of an exemplary system for occluding an atrial appendage of the present disclosure.
Figure 12:
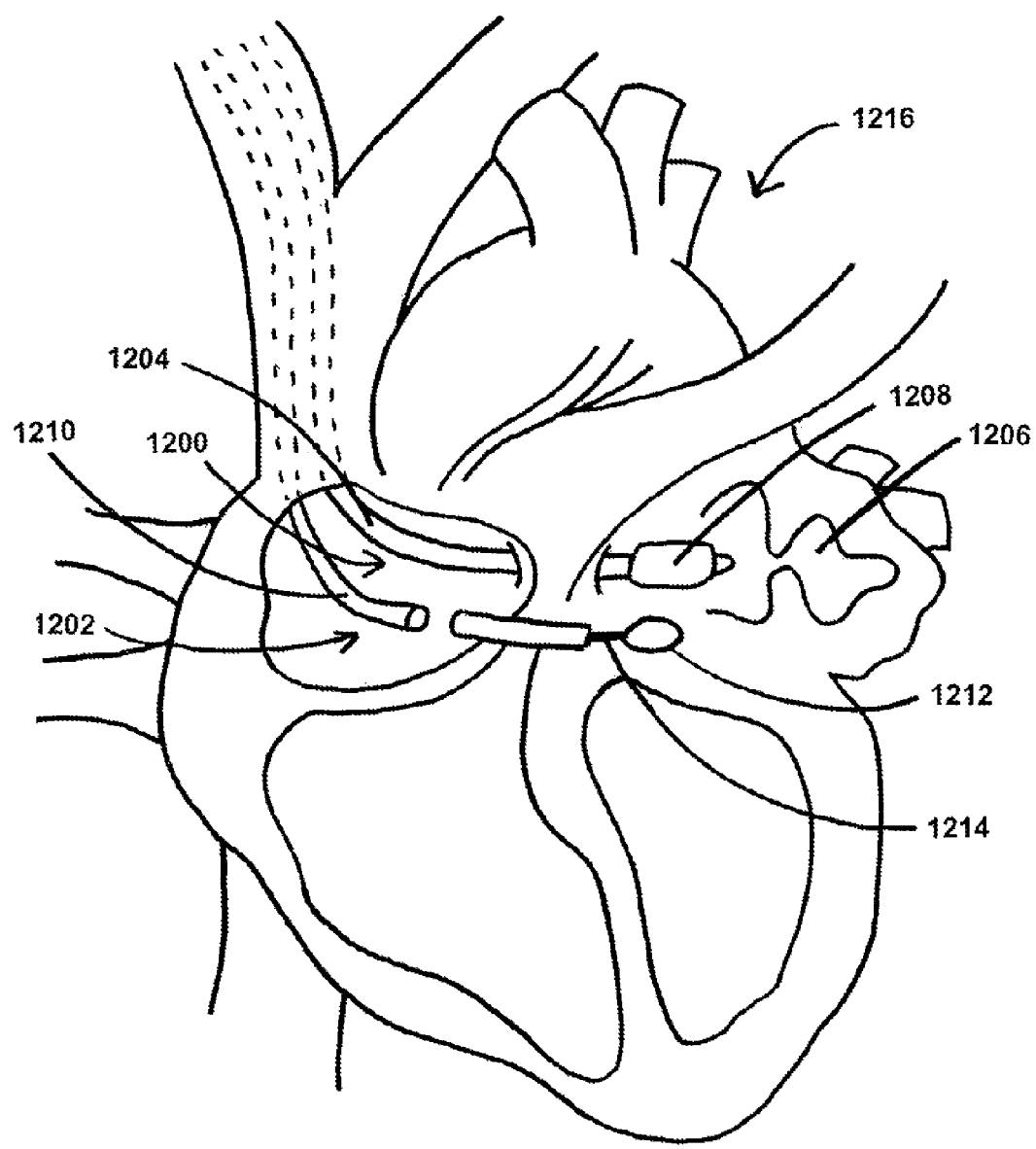
FIG. 12 shows a view of a heart with an exemplary system for occluding an atrial appendage of the present disclosure positioned therein.

In at least an additional embodiment of a system for occluding the LAA of the disclosure of the present application, the system involves the use of two devices to perform an exemplary LAA occlusion procedure. As shown in FIGS. 10 and 12, an exemplary system 1600 comprises a first device 1200 and a second device 1202. In at least one embodiment, first device 1200 comprises a tube 1204 and a balloon 1208 coupled to tube 1204, wherein the balloon 1208 is sized and shaped for insertion into the LAA cavity 1206. In at least one exemplary embodiment, tube 1204 of first device 1200 may comprise a transseptal balloon catheter. Balloon 1208, to perform the LAA occlusion procedure as disclosed in further detail herein, would be capable of inflation and deflation. Second device 1202, in an exemplary embodiment, comprises a tube 1210 sized and shaped for insertion into a patient, with the tube 1210 comprising a lumen extending at least partially from the distal end to the proximal end of tube 1210. Second device 1202, in an exemplary embodiment, further comprises a loop 1212 sized and shaped to fit at least partially within the lumen of tube 1210, wherein loop 1212 is capable of protraction from the distal end of tube 1210. Loop 1212 may optionally be coupled to a shaft 1214 at or near the distal end of shaft 1214, whereby movement of shaft 1214, when positioned with tube 1210, would allow loop 1212 to protract and/or retract from the distal end (opening) of tube 1210. Tube 1210 may comprise and/or function as an engagement catheter, and the loop 1212/shaft 1214 portion of second device 1202 may comprise and/or function as a delivery catheter. First device 1200 and/or second device 1202 may be introduced into heart 1216 as described in detail herein.

Figure 11:
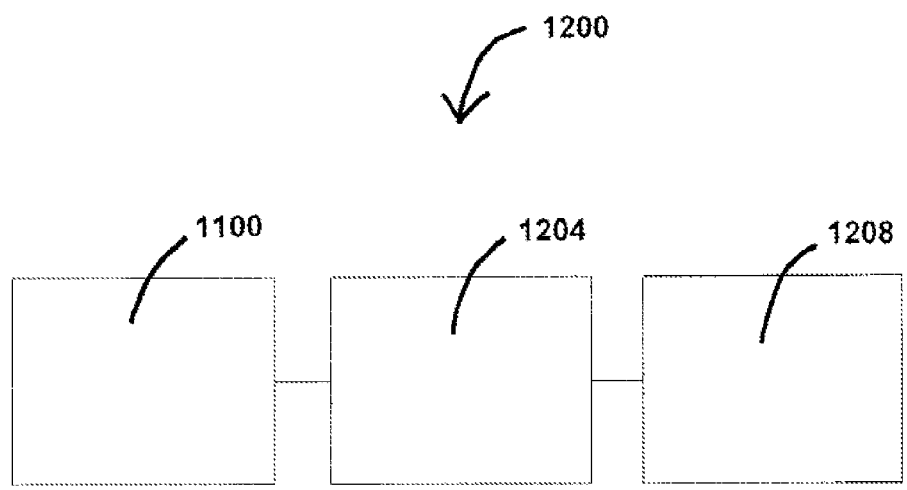
FIG. 11 shows an exemplary embodiment of a first device of an exemplary system for occluding an atrial appendage of the present disclosure.

An exemplary embodiment of a portion of a system for occluding an atrial appendage of the present disclosure is shown in FIG. 11. As shown in FIG. 11, and in an exemplary embodiment, first device 1200 may comprise a suction/inflation source 1100 operably coupled to tube 1204, whereby operation of the suction/inflation source 1100 may facilitate the inflation and/or deflation of balloon 1208 coupled thereto.

Suction/inflation source 1100 may also operate to remove blood from an atrial appendage as referenced herein regarding the description of FIG. 15C.

In at least an additional embodiment of a method for occluding the LAA of the disclosure of the present application, the method involves the use of first device 1200 and second device 1202 to perform the occlusion procedure. As shown in FIG. 13A, at least one step of a method for occluding an LAA 1300 comprises the introduction of first device 1200 into a heart and advancement of first device 1200 into the right atrium 1302 of the heart. Such an introduction may be performed under local anesthesia, and may also use conscious sedation techniques as known in the art. First device 1200 may be introduced into the body using femoral or jugular venous puncture and then progressing first device into the right atrium 1302 of the heart. The introduction of first device 1200 into the body may be performed using transesophageal echocardiography and fluoroscopy so that the user of first device 1200 is able to advance first device 1200 into the right atrium 1302 of the heart.

After first device 1200 is positioned within the right atrium 1302 of the heart, transseptal puncture at the level of the fossa ovalis area may be performed to advance at least a portion of first device 1200 through the atrial septum 1304 of the heart into the left atrium 1306 of the heart as shown in FIG. 13A. The step of transseptal puncture may be performed using a standard transseptal sheath kit as known in the art. The administration of heparin to the patient prior to transseptal puncture may increase the activated clotting time above 250 seconds.

As shown in FIG. 13A, a portion of first device 1200 has advanced through a puncture within atrial septum 1304, and balloon 1208 of first device 1200 has been positioned within the LAA cavity 1206. The distal end of first device 1200 may be advanced into the LAA cavity 1206 by the use of a guide wire (not shown) using procedures known in the art, for example, to advance catheters within a body with the use of a guide wire.

At least one additional step of a method to perform an LAA occlusion of the present disclosure involves the inflation of balloon 1208 as shown in FIG. 13B. As shown in FIG. 13B, balloon 1208 has been inflated to occupy most or all of the LAA cavity 1206 and to displace blood present within the LAA cavity 1206 prior to inflation. Balloon 1208 may be inflated using an inflation/suction source (shown in FIG. 11) operably coupled to tube 1204 of first device 1200, whereby introduction of a gas and/or a liquid from the inflation/suction source 1100 through the lumen of tube 1204 into balloon 1208 coupled to tube 1204 causes balloon 1208 to inflate/expand. To facilitate such inflation/expansion, at least one aperture (not shown) would be defined within a portion of tube 1204 surrounded by balloon 1208 so that a gas and/or a liquid present within the lumen of tube 1204 would be able to enter balloon 1208. Similarly, the deflation of balloon 1208, as described in further detail below, may be facilitated using suction generated by the inflation/suction source 1100 to remove at least a portion of the gas and/or liquid present within an inflated balloon 1208.

As shown in FIG. 13B, loop 1212 of second device 1202 is capable of encircling LAA 1300 while balloon 1208 of first device 1200 is inflated within the LAA cavity. Second device 1202 may be introduced into the patient using similar techniques as described herein for the introduction of first device 1200. After at least a portion of second device 1202 has entered the heart or approached the area of the heart, the distal end of second device 1202 could be advanced into the pericardial sac using methods known in the art for the introduction of second device 1202, or a portion of second device 1202, as described herein. For example, second device 1202 may comprise an engagement catheter and a delivery catheter/mechanism, wherein the engagement catheter engages a heart wall, allowing the delivery catheter/mechanism to puncture the heart wall and enter into the pericardial space, in at least one exemplary embodiment, at least a portion of second device 1202, comprising loop 1212 coupled to shaft 1214, may enter into the pericardial space 1308 as shown in FIG. 13B. Loop 1212 may then be used to encircle LAA 1300 as shown in FIG. 13B by maneuvering shaft 1214 so that loop 1212 encircles and engages LAA 1300. In at least one embodiment, balloon 1208 is kept inflated while loop 1212 is positioned around LAA 1300 as shown in FIG. 13B.

After loop 1212 has encircled and engaged LAA 1300, loop 1212 may be tightened around LAA 1300 as shown in FIG. 13C to facilitate LAA 1300 occlusion. As shown in FIG. 13C, loop 1212 has been tightened around LAA 1300 during or after the deflation of balloon 1208 and removal of the portion of first device 1200 present within LAA cavity 1206 while balloon 1208 was inflated. After loop 1212 has been tightened around LAA 1300, loop 1212 is separated from shaft 1214, or from the portion of second device 1202 to which loop 1212 is connected, so that second device 1202 may be removed from the body. Loop 1212 may be separated from the remainder of second device 1202 by, for example, the use of an electromagnetic current to separate loop 1212, a turning maneuver (clockwise or counterclockwise) to separate loop 1212, or other means known in the art to separate a portion of a device from the remainder of the device.

After the portion of first device 1200 previously present within LAA cavity 1206 has been removed from LAA cavity 1206, first device 1200 may be retracted through the puncture within atrial septum 1304, and may be completely removed from the body from, for example, the original femoral or jugular venous puncture site. Second device 1202 may be removed from the body, either before, during, or after the removal of first device 1200, with the portion of second device 1202 present within the pericardial space 1308 of the heart being removed from the pericardial space 1308 from the original site of entry into the pericardial space 1308. An anti-platelet adhesive treatment may be provided to the patient during or after the procedure to facilitate heart healing from trauma incurred during the procedure to facilitate LAA occlusion.

It can be appreciated that one or more of the aforementioned steps may be performed in an order not explicitly disclosed above. For example, the placement of loop 1212 around the LAA 1300 may be performed prior to the inflation of balloon 1208.

Figure 14:
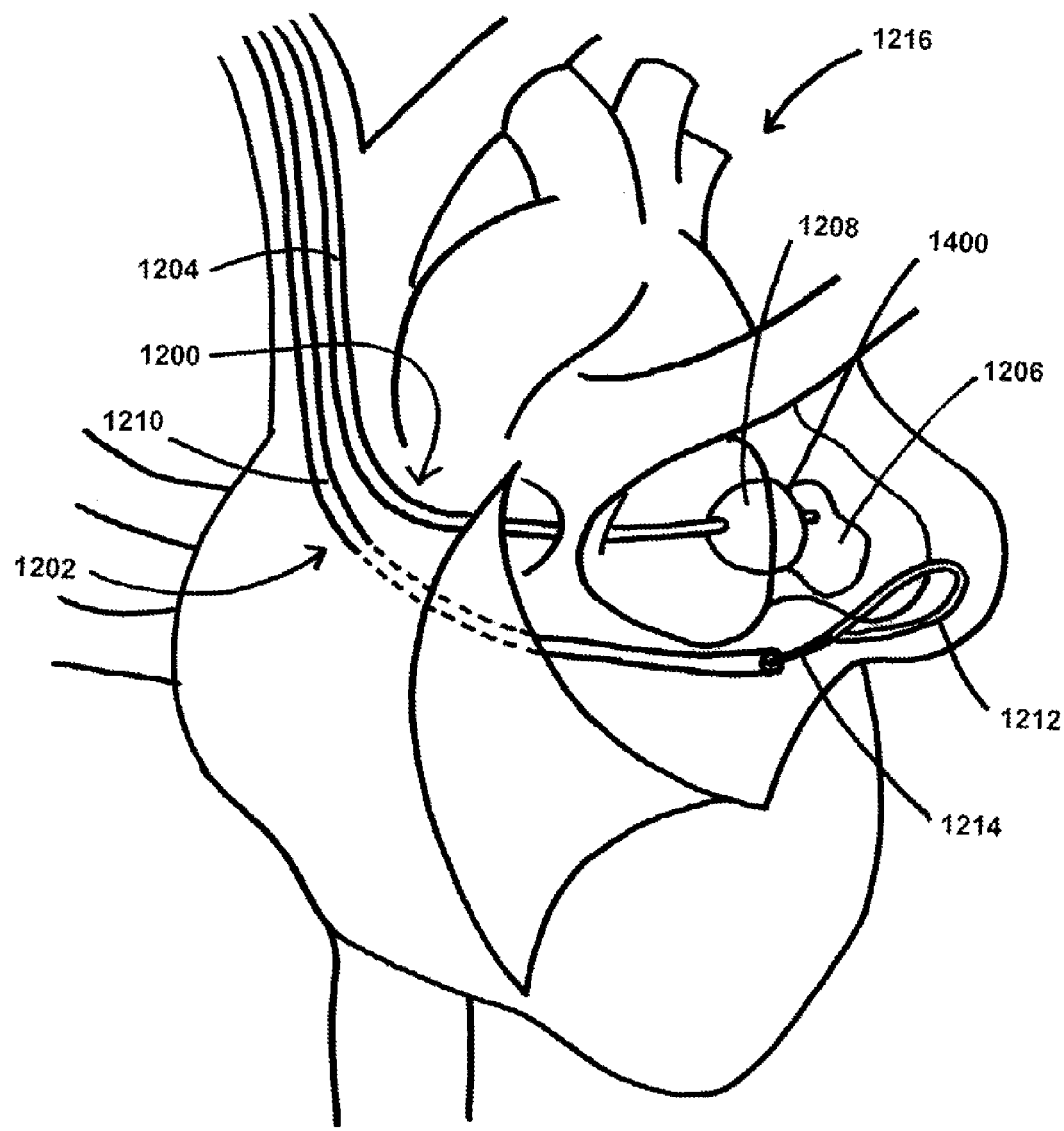
FIG. 14 shows another view of a heart with an exemplary system for occluding an atrial appendage of the present disclosure positioned therein.

In at least another embodiment of a system for occluding the LAA of the disclosure of the present application, the system also involves the use of two devices to perform an exemplary LAA occlusion procedure. As shown in FIG. 14, an exemplary system comprises a first device 1200 and a second device 1202. In at least one embodiment, first device 1200 comprises a tube 1204 and a balloon 1208 coupled to tube 1204, wherein the balloon 1208 is sized and shaped for insertion into an entrance of the LAA cavity 1400 rather than entry of most or all of balloon 1208 into LAA cavity 1206. In at least one exemplary embodiment, tube 1204 of first device 1200 may comprise a transseptal balloon catheter. Balloon 1208, to perform the LAA occlusion procedure as disclosed in further detail herein, would be capable of inflation and deflation.

Second device 1202, in an exemplary embodiment, comprises a tube 1210 sized and shaped for insertion into a patient, with the tube 1210 comprising a lumen extending at least partially from the distal end to the proximal end of tube 1210. Second device 1202, in an exemplary embodiment, further comprises a loop 1212 sized and shaped to fit at least partially within the lumen of tube 1210, wherein loop 1212 is capable of protraction from the distal end of the tube 1210. Loop 1212 may be coupled to a shaft 1214 at or near the distal end of shaft 1214, whereby movement of shaft 1214, when positioned with tube 1210, would allow loop 1212 to protract and/or retract from the distal end (opening) of tube 1210. Tube 1210 may comprise and/or function as an engagement catheter, and the loop 1212/shaft 1214 portion of second device 1202 may comprise and/or function as a delivery catheter. First device 1200 and/or second device 1202 may be introduced into heart 1216 as described in detail herein.

In at least an additional embodiment of a method for occluding the LAA of the disclosure of the present application, the method involves the use of first device 1200 and second device 1202 to perform the occlusion procedure. As shown in FIG. 15A, at least one step of a method for occluding an LAA 1300 comprises the introduction of first device 1200 into a heart and advancement of first device 1200 into the right atrium 1302 of the heart. Such an introduction may be performed under local anesthesia, and may also use conscious sedation techniques as known in the art. First device 1200 may be introduced into the body using femoral or jugular venous puncture and then progressing first device 1200 into the right atrium 1302 of the heart. The introduction of first device 1200 into the body may be performed using transesophageal echocardiography and fluoroscopy so that the user of first device 1200 is able to advance first device 1200 into the right atrium 1302 of the heart.

After first device 1200 is positioned within the right atrium 1302 of the heart, transseptal puncture at the level of the fossa ovalis area may be performed to advance at least a portion of first device 1200 through the atrial septum 1304 of the heart into the left atrium 1306 of the heart as shown in FIG. 15A. The step of transseptal puncture may be performed using a standard transseptal sheath kit as known in the art. The administration of heparin to the patient prior to transseptal puncture may increase the activated clotting time above 250 seconds.

As shown in FIG. 15A, a portion of first device 1200 has advanced through a puncture within atrial septum 1304, and balloon 1208 of first device 1200 has been positioned at the entrance of the LAA cavity 1400. The distal end of first device 1200 may be advanced to the entrance of the LAA cavity 1400 by the use of a guide wire (not shown) using procedures known in the art, for example, to advance catheters within a body with the use of a guide wire.

At least one additional step of a method to perform a LAA occlusion of the present disclosure involves the inflation of balloon 1208 as shown in FIG. 15B. As shown in FIG. 15B, balloon 1208 has been inflated to occlude the entrance of the LAA cavity 1400, whereby suction from an inflation/suction source 1100 (shown in FIG. 11) operably coupled to tube 1204 of first device 1200 allows blood present within the LAA cavity prior to occlusion of the entrance of the LAA cavity 1400 to be removed, facilitating the effective collapse of LAA cavity 1206. Balloon 1208 may be inflated using an inflation/suction source 1100 (shown in FIG. 11) operably coupled to tube 1204 of first device 1200, whereby introduction of a gas and/or a liquid from the inflation/suction source 1100 through the lumen of tube 1204 into balloon 1208 coupled to tube 1204 causes balloon 1208 to inflate/expand. To facilitate such inflation/expansion, at least one aperture (not shown) would be defined within a portion of tube 1204 surrounded by balloon 1208 so that a gas and/or a liquid present within the lumen of tube 1204 would be able to enter balloon 1208. Similarly, the deflation of balloon 1208, as described in further detail below, may be facilitated using suction generated by the inflation/suction source 1100 to remove at least a portion of the gas and/or liquid present within an inflated balloon 1208.

As shown in FIG. 15B, loop 1212 of second device 1202 is capable of encircling LAA 1300 while balloon 1208 of first device 1200 is inflated to occlude the entrance of the LAA cavity 1400. Second device 1202 may be introduced into the patient using similar techniques as described herein for the introduction of first device 1200. After at least a portion of second device 1202 has entered the heart or approached the area of the heart, the distal end of second device 1202 could be advanced into the pericardial space using methods known in the art for the introduction of second device 1202, or a portion of second device 1202, as described herein. For example, second device 1202 may comprise an engagement catheter and a delivery catheter/mechanism, wherein the engagement catheter engages a heart wall, allowing the delivery catheter/mechanism to puncture the heart wall and enter into the pericardial space. In at least one exemplary embodiment, at least a portion of second device 1202, comprising loop 1212 coupled to shaft 1214, may enter into the pericardial space 1308 as shown in FIG. 15B. Loop 1212 may then be used to encircle LAA 1300 as shown in FIG. 15B by maneuvering shaft 1214 so that loop 1212 encircles and engages LAA 1300. In at least one embodiment, balloon 1208 is kept inflated while loop 1212 is positioned around LAA 1300 as shown in FIG. 15B.

After loop 1212 has encircled and engaged LAA 1300, loop 1212 may be tightened around LAA 1300 as shown in FIG. 15C to facilitate LAA 1300 occlusion. As shown in FIG. 15C, loop 1212 has been tightened around LAA 1300 during or after the deflation of balloon 1208 and removal of the portion of first device 1200 present within LAA cavity 1206 while balloon 1208 was inflated. After loop 1212 has been tightened around LAA 1300, loop 1212 is separated from shaft 1214, or from the portion of second device 1202 to which loop 1212 is connected, so that second device 1202 may be removed from the body. Loop 1212 may be separated from the remainder of second device 1202 by, for example, the use of an electromagnetic current to separate loop 1212, a turning maneuver (clockwise or counterclockwise) to separate loop 1212, or other means known in the art to separate a portion of a device from the remainder of the device.

After the portion of first device 1200 previously occluding the entrance of the LAA cavity 1400 has been removed, first device 1200 may be retracted through the puncture within atrial septum 1304, and may be completely removed from the body from, for example, the original femoral or jugular venous puncture site. Second device 1202 may be removed from the body, either before, during, or after the removal of first device 1200, with the portion of second device 1202 present within the pericardial space 1308 of the heart being removed from the pericardial space 1308 from the original site of entry into the pericardial space 1308. An anti-platelet adhesive treatment may be provided to the patient during or after the procedure to facilitate heart healing from any trauma incurred during the procedure to facilitate LAA occlusion.

Figure 16A:
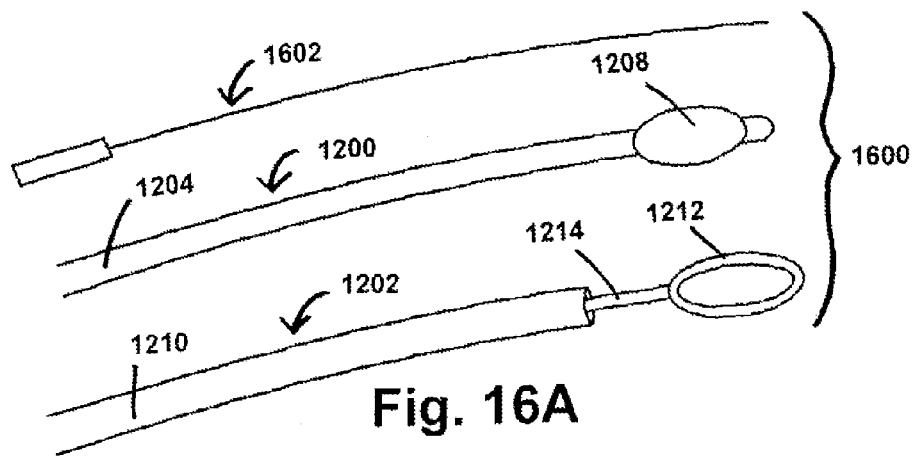
FIGS. 16A and 16B show exemplary embodiments of systems for occluding an atrial appendage of the present disclosure.
Figure 16B:
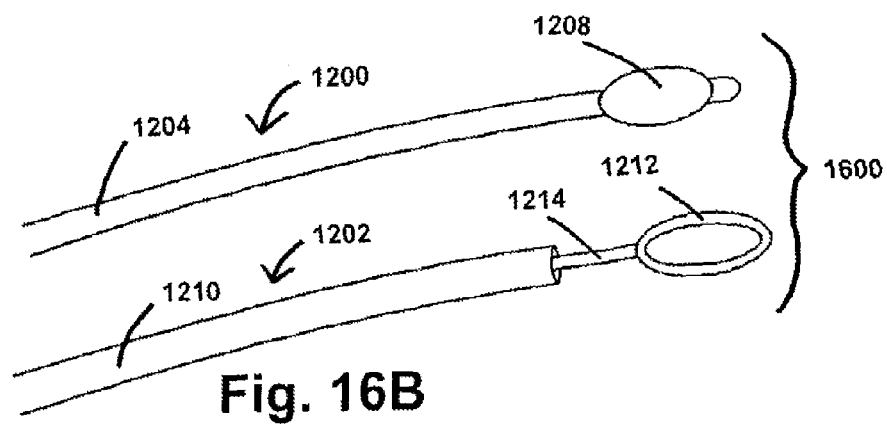

Exemplary systems for occluding an LAA are shown in FIGS. 16A and 16B. As shown in FIG. 16A, system 1600 comprises a guide wire 1602, a first device 1200, and a second device 1202. In this exemplary embodiment, first device 1200 comprises tube 1204 and balloon 1208 coupled thereto, and second device 1202 comprises tube 1210, loop 1212, and shaft 1214. This exemplary system 1600 may be used to perform the steps for occluding an LAA as disclosed in detail herein. In an additional embodiment, second device 1202 may comprise tube 1210 and loop 1212, but not shaft 1214.

An additional exemplary embodiment of a system for occluding an LAA is shown in FIG. 16B. As shown in FIG. 16B, system 1600 comprises a first device 1200 and a second device 1202, and in this exemplary embodiment, first device 1200 comprises tube 1204 and balloon 1208 coupled thereto, and second device 1202 comprises tube 1210, loop 1212, and shaft 1214. In this exemplary embodiment, system 1600 does not include guide wire 1602.

Figure 16C:
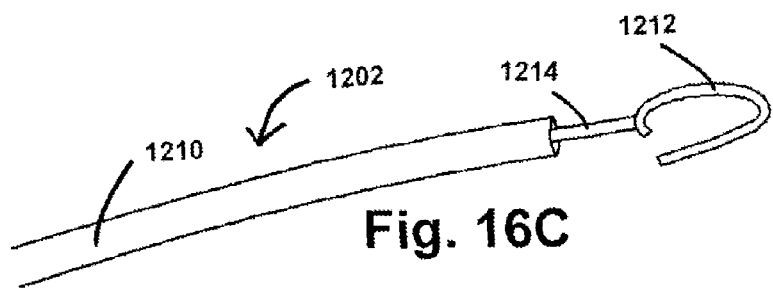
FIG. 16C shows an exemplary embodiment of a second device of an exemplary system for occluding an atrial appendage of the present disclosure.

Another exemplary embodiment of a second device 1202 is shown in FIG. 16C. As shown in FIG. 16C, second device 1202 comprises tube 1210, loop 1212, and shaft 1214. In this exemplary embodiment, loop 1212 is not a permanently "closed" loop, which may facilitate the encircling of an atrial appendage prior to closing said loop 1212.

Many benefits and advantages to using systems and performing methods of the present disclosure exist, noting that said procedures are minimally invasive and may be used by all patients regardless of patient age and/or condition. Such methods avoid the need for surgery and further avoid the need of intracardiac or other implantable devices. In addition, the devices comprising the systems of the present disclosure replace the use of other oversized devices (which may be, for example, 20% to 50% larger than the ostium of an LAA as measured by angiography and other methods), which prevents the risk of LAA tissue overdistentation (circumflex coronary artery distortion or compression). Such procedures also avoid the possible leakage around the devices, the risk of thrombus formation, and the migration, erosion, or perforation of the LAA. In addition to the foregoing, said methods also avoid mitral valve damage, pulmonary venous obstruction, the risk of infections endocarditis, and the use of anti-coagulation therapy.

While various embodiments of devices, systems, and methods for occluding an atrial appendage have been described in considerable detail herein, the embodiments are merely offered by way of non-limiting examples. Many variations and modifications of the embodiments described herein will be apparent to one of ordinary skill in the art in light of the disclosure. It will therefore be understood by those skilled in the art that various changes and modifications may be made, and equivalents may be substituted for elements thereof, without departing from the scope of the disclosure. Indeed, this disclosure is not intended to be exhaustive or to limiting. The scope of the disclosure is to be defined by the appended claims, and by their equivalents.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations on the claims. In addition, the claims directed to a method and/or process should not be limited to the performance of their steps in the order written, and one skilled in the art can readily appreciate that the sequences may be varied and still remain within the spirit and scope of the present disclosure.

It is therefore intended that this description and the appended claims will encompass, all modifications and changes apparent to those of ordinary skill in the art based on this disclosure.

The invention claimed is:

1. A method for occluding an atrial appendage of a heart, the method comprising the steps of:
    percutaneously introducing at least a portion of a first device into a vein of a patient and advancing the same through the vein, into a right atrium, and ultimately into an atrial appendage cavity of a heart, the first device comprising:
        a first tube having a distal end; and
        a balloon capable of inflation and deflation, the balloon coupled to the first tube at or near the distal end of the first tube;
    percutaneously introducing at least a portion of a second device into the vein and advancing the same through the vein, into the right atrium, and ultimately into a pericardial space surrounding the heart from inside the heart by engaging a targeted tissue on an interior wall of the heart, puncturing the tissue using the second device, and advancing a distal end of the second device through the punctured targeted tissue and into the pericardial space, the second device comprising:
        a second tube sized and shaped for insertion into the pericardial space surrounding the heart, the second tube comprising a lumen extending at least partially from a second tube distal end to a second tube proximal end; and
        a loop sized and shaped to fit at least partially within the lumen of the second tube, wherein the loop is capable of protraction from the second tube distal end;
    positioning the balloon of the first device at least partially within the atrial appendage cavity;
    inflating the balloon to displace blood present within the atrial appendage cavity;
    positioning the loop of the second device around the atrial appendage;
    tightening the loop around the atrial appendage;
    deflating the balloon to allow for ultimate removal of the first device from the atrial appendage cavity; and
    separating the loop from the second device so that the loop remains positioned and tightened around the atrial appendage.

2. The method of claim 1, further comprising the step of:
    removing the first device from the heart.

3. The method of claim 1, further comprising the step of:
    removing the second tube from the pericardial space surrounding the heart.

4. The method of claim 3, further comprising the step of providing the patient with an anti-platelet adhesive treatment.

5. The method of claim 1, wherein the step of introducing at least a portion of a first device into an atrial appendage cavity is performed after the patient has been administered local anesthesia.

6. The method of claim 5, wherein the step of introducing at least a portion of a first device into an atrial appendage cavity is performed after the patient has been administered a sedative allowing the patient to remain conscious as the method for occluding the atrial appendage is performed.

7. The method of claim 1, wherein the step of introducing at least a portion of a first device into an atrial appendage cavity and the step of introducing at least a portion of the second device into a pericardial space surrounding the heart are performed using transesophageal echocardiography and fluoroscopy.

8. The method of claim 1, wherein the step of introducing at least a portion of a first device into an atrial appendage cavity is performed by inserting at least a portion of the first device into the patient using femoral venous puncture and advancing at least a portion of the first device to the heart.

9. The method of claim 1, wherein the step of introducing at least a portion of a first device into an atrial appendage cavity is performed by inserting at least a portion of the first device into the patient using jugular venous puncture and advancing the first device to the heart.

10. The method of claim 1, wherein the step of introducing at least a portion of a first device into an atrial appendage cavity involves a transseptal puncture from a right atrium to a left atrium of the heart.

11. The method of claim 10, wherein the patient is administered heparin prior to the transseptal puncture.

12. The method of claim 1, wherein the step of introducing at least a portion of a first device into an atrial appendage cavity is performed using a guide wire.

13. The method of claim 1, wherein the step of deflating the balloon allows the loop to further tighten around the atrial appendage.

14. The method of claim 1, wherein the step of separating the loop from the second device is performed using an electromagnetic current.

15. The method of claim 1, wherein the step of separating the loop from the second device is performed by twisting the second device in a direction to allow the loop to separate from the second device.

16. The method of claim 1, wherein the balloon is sized and shaped for insertion into the atrial appendage cavity.

17. The method of claim 1, wherein the atrial appendage is a left atrial appendage.

18. The method of claim 1, wherein the second device further comprises a shaft having a distal end, wherein the loop is coupled to the shaft at or near the distal end of the shaft.

19. The method of claim 1, wherein at least one aperture is defined within the first tube at or near the balloon, and wherein the step of inflating the balloon is performed using an inflation source operably coupled to the first tube.

20. A method for occluding an atrial appendage of a heart of a patient, the method comprising the steps of:
  providing a first device, the first device comprising:
    a first tube having a distal end; and
    a balloon capable of inflation and deflation, the balloon coupled to the first tube at or near the distal end of the first tube, the balloon sized and shaped for insertion into a left atrial appendage cavity;
  providing a second device, the second device comprising:
    a second tube sized and shaped for insertion into a pericardial space surrounding the heart, the second tube comprising a lumen extending at least partially from a second tube distal end to a second tube proximal end;
    a loop sized and shaped to fit at least partially within the lumen of the second tube, wherein the loop is capable of protraction from the second tube distal end; and
    a shaft having a distal end, wherein the loop is coupled to the shaft at or near the distal end of the shaft;
  introducing the first device into the patient using femoral or jugular venous puncture;
  advancing the first device within the patient from a site of femoral or jugular venous puncture so that the distal end of the first tube of the first device is positioned within a right atrium of the heart;
  puncturing a septum between the right atrium and a left atrium of the heart using the first device;
  advancing the distal end of the first tube of the first device through the punctured septum;
  positioning the distal end of the first tube within the left atrial appendage cavity so that the balloon is at least partially positioned within the left atrial appendage cavity;
  introducing the second device into the patient using femoral or jugular venous puncture;
  advancing the second device within the patient to a location at or near a targeted tissue on an interior wall of the heart;
  puncturing the targeted tissue using the second device;
  advancing the distal end of the second tube of the second device from inside the heart through the punctured targeted tissue into a pericardial space to a location at or near the left atrial appendage;
  inflating the balloon to displace blood present within the left atrial appendage cavity;
  positioning the loop of the second device around the left atrial appendage;
  tightening the loop around the left atrial appendage;
  deflating the balloon to allow for ultimate removal of the first device from the left atrial appendage cavity; and
  separating the loop from the shaft so that the loop remains positioned and tightened around the left atrial appendage.

* * * * *